(12) United States Patent
Rachford et al.

(10) Patent No.: US 11,746,184 B2
(45) Date of Patent: *Sep. 5, 2023

(54) POLYIMIDE-POLYARYLENE POLYMERS

(71) Applicant: Rohm and Haas Electronic Materials LLC, Marlborough, MA (US)

(72) Inventors: Aaron A. Rachford, South Grafton, MA (US); Charles R. Kinzie, Boston, MA (US); Michael K. Gallagher, Hopkinton, MA (US); Christopher Gilmore, Natick, MA (US); Young-Seok Kim, San Jose, CA (US)

(73) Assignee: ROHM AND HAAS ELECTRONIC MATERIALS LLC, Marlborough, MA (US)

( * ) Notice: Subject to any disclaimer, the term of this patent is extended or adjusted under 35 U.S.C. 154(b) by 301 days.

This patent is subject to a terminal disclaimer.

(21) Appl. No.: 17/088,817

(22) Filed: Nov. 4, 2020

(65) Prior Publication Data

US 2021/0147616 A1 May 20, 2021

Related U.S. Application Data

(60) Provisional application No. 62/937,405, filed on Nov. 19, 2019.

(51) Int. Cl.
| | | |
|---|---|---|
| *C08G 61/12* | (2006.01) | |
| *C07D 403/10* | (2006.01) | |
| *C07D 487/04* | (2006.01) | |
| *C07D 495/14* | (2006.01) | |
| *C07D 498/04* | (2006.01) | |

(52) U.S. Cl.
CPC .......... *C08G 61/124* (2013.01); *C07D 403/10* (2013.01); *C07D 487/04* (2013.01); *C07D 495/14* (2013.01); *C07D 498/04* (2013.01)

(58) Field of Classification Search
CPC .. C08G 61/124; C07D 403/10; C07D 487/04; C07D 495/14; C07D 498/04
See application file for complete search history.

(56) References Cited

U.S. PATENT DOCUMENTS

| 5,965,679 | A | 10/1999 | Godschalx et al. |
| 6,121,495 | A | 9/2000 | Babb et al. |
| 6,288,188 | B1 | 9/2001 | Godschalx et al. |
| 6,646,081 | B2 | 11/2003 | Godschalx et al. |
| 7,678,873 | B1 * | 3/2010 | Tan .................... C08G 73/1046 528/128 |
| 8,653,512 | B2 | 2/2014 | Auman et al. |
| 2006/0252906 | A1 | 11/2006 | Godschalx et al. |
| 2010/0240908 | A1 | 9/2010 | Imakuni et al. |
| 2017/0009006 | A1 | 1/2017 | Ding et al. |
| 2018/0162968 | A1 | 6/2018 | Kinzie et al. |
| 2018/0171069 | A1 | 6/2018 | Wang et al. |

FOREIGN PATENT DOCUMENTS

| FR | 2428655 A1 | 1/1980 |
| WO | 2017222291 A2 | 2/2018 |

OTHER PUBLICATIONS

Kumar et al., "Hybrid Polyimide-Polyphenylenes by the Diels-Alder Polymerization Between Biscyclopentadienones and Ethynyl-Terminated Imides", Microelectronics Technology ACS Symposium Series, Chapter 34, 1995, pp. 518-526.
Search report for corresponding European Application No. 20 20 6558 dated Apr. 6, 2021.
Kumar, et al., "Hybrid polyimide-polyphenylenes by the Diels-Alder polymerization between biscyciopentadienones, and ethynyl-terminated imides", Microelectronics Technology; ACS Symposium Series, 1995, Chapter 34, pp. 518-526.
Likhatchev, et al, "Soluble aromatic polyimides based on 2,2-bis(3-amino-4-hydroxyphenyl) hexafluoropropane: synthesis and properties", Journal of Applied Polymer Science, 1996, vol. 59, pp. 725-735.
Guzman-Lucero, et al., "Imide-to-benzoxazole rearrangement in ortho substituted poly(4-4'-diphenylene pyrometallitimide)s", Polymer Bulletin, 2002, vol. 48, pp. 261.
Likhatchev, "Chemistry and properties of o-hydorxy—and o-amino-substituted polyimides in polyimides and other high temperature polymers", VSP, Utrecht, Netherlands, 2002, p. 79.
Tulllos, et al., "Unexpected thermal conversion of hydroxy-containing polyimides to polybenzoxazoles", Polymer, 1999, vol. 40, pp. 3463.
Kardash, et al., "The thermal degradation of aromatic polybenzoxazoles", Polymer Science USSR, 1969, vol. 11, No. 9, pp. 2276.

* cited by examiner

*Primary Examiner* — Shane Fang
(74) *Attorney, Agent, or Firm* — G. Creston Campbell

(57) ABSTRACT

Disclosed is a bis-imide compound comprising two or more aryl moieties substituted with ethynyl moieties and the two or more aryl moieties each having one or more polar substituents. Further disclosed is a polymer composition comprising a copolymer polymerized from a monomer mixture of (a) one or more first monomers comprising a bis-imide compound comprising two or more aryl moieties substituted with ethynyl moieties and the two or more aryl moieties each having one or more polar substituents; and (b) one or more second monomers comprising two or more cyclopentadienone moieties. The polymer compositions exhibit favorable properties for use in electronics and displays applications.

5 Claims, No Drawings

POLYIMIDE-POLYARYLENE POLYMERS

BACKGROUND OF THE INVENTION

1. Field of the Disclosed and Claimed Inventive Concepts

The presently disclosed process(es), procedure(s), method(s), product(s), result(s), and/or concept(s) (collectively referred to hereinafter as the "present disclosure") relate generally to novel organic compounds that can be used as monomeric components for making polymers. In particular, functionalized bis-imide compounds can be copolymerized with cyclopentadienone-containing species to produce polymers with properties that are well suited for electronics and displays applications.

2. Background and Applicable Aspects of the Presently Disclosed and Claimed Inventive Concept(s)

Polymers are increasingly used in electronics and displays applications as a result of their widely-variable properties and processability advantages over more-conventional incumbent materials. Polyphenylene polymers represent one such class of materials. They can be made to exhibit an effective combination of good chemical resistance, high $T_g$, and mechanical toughness that are required in many electronics and displays applications. Further, polyphenylene polymer molecular weight and solution concentration may be adjusted to enable precise and convenient deposition by spin-coating, a universally-important industrial processing method. The aromatic hydrocarbon structure of the cured film provides low dielectric constant, high thermal stability, and low moisture absorption. The synthetic flexibility afforded by heteroatom inclusion, copolymer formation, and the like makes available families of materials that can be prepared for highly-specific applications in-use.

Polyimides are another class of polymeric materials that have found wide-ranging uses in electronics and displays applications since they were first introduced (see, for example, U.S. Pat. No. 8,653,512 B2). These materials can exhibit low dielectric constants, low moisture absorption, high $T_g$, good thermal stability, low coefficient of thermal expansion (CTE), excellent chemical resistance, and flexible processability.

Given the importance of these two classes of polymeric materials, efforts have been made to produce hybrid polyphenylene-polyimide polymers for use in electronics and displays applications. The polyphenylenes are generally recognized for their contribution of favorably-low dielectric constants, while polyimides can contribute highly modular and tunable thermal and mechanical properties. The two classes of materials can be combined into a single, unbranched polymer chain that can exhibit the strengths of both polymer types with hybrid properties that are tunable to particular end-uses electronics and displays applications. Polyphenylene-polyimide polymers are further known to exhibit spin- and slot-die coater compatibility, high coating uniformity, low defect and surface roughness, low outgassing, short cure time, and low stress-after-cure, and other useful properties. The films associated with these compositions can be prepared which exhibit a high degree of flexibility and toughness, high elongation, and thermal stability at the high temperatures associated with processing conditions typical in electronics and displays applications.

More widespread industrial use of polyphenylene-polyimide polymers can be limited, however, by the relative insolubility of typical compositions in solvent systems commonly used in electronics and displays applications. Certain polar, protic solvent systems, for example, are ineffective at solubilizing polyphenylene-polyimide polymers. Prior work has thus been directed at improving the solubility of polyphenylene-polyimide polymers in such industrially-important solvents while maintaining the overall materials' advantages. The use of lower-molecular-weight polymers and/or the functionalization of monomers have both found limited success in this regard.

There is thus a continuing need for new polyphenylene-polyimide polymers that display enhanced solubility in polar, protic solvents while retaining the properties that make them useful in electronics and displays applications.

DETAILED DESCRIPTION

Before explaining at least one embodiment of the present disclosure in detail, it is to be understood that the present disclosure is not limited in its application to the details of construction and the arrangement of the components or steps or methodologies set forth in the following description. The present disclosure is capable of other embodiments or of being practiced or carried out in various ways. Also, it is to be understood that the phraseology and terminology employed herein is for the purpose of description and should not be regarded as limiting.

Unless otherwise defined herein, technical terms used in connection with the present disclosure shall have the meanings that are commonly understood by those of ordinary skill in the art. Further, unless otherwise required by context, singular terms shall include pluralities and plural terms shall include the singular.

All patents, published patent applications, and non-patent publications mentioned in the specification are indicative of the level of skill of those skilled in the art to which the present disclosure pertains. All patents, published patent applications, and non-patent publications referenced in any portion of this application are herein expressly incorporated by reference in their entirety to the same extent as if each individual patent or publication was specifically and individually indicated to be incorporated by reference.

All of the articles and/or methods disclosed herein can be made and executed without undue experimentation in light of the present disclosure. While the articles and methods of the present disclosure have been described in terms of preferred embodiments, it will be apparent to those of ordinary skill in the art that variations may be applied to the articles and/or methods and in the steps or in the sequence of steps of the method(s) described herein without departing from the concept, spirit and scope of the present disclosure. All such similar substitutes and modifications apparent to those skilled in the art are deemed to be within the spirit, scope and concept of the present disclosure.

As utilized in accordance with the present disclosure, the following terms, unless otherwise indicated, shall be understood to have the following meanings.

The use of the word "a" or "an" when used in conjunction with the term "comprising" may mean "one," but it is also consistent with the meaning of "one or more," "at least one," and "one or more than one." The use of the term "or" is used to mean "and/or" unless explicitly indicated to refer to alternatives only if the alternatives are mutually exclusive, although the disclosure supports a definition that refers to only alternatives and "and/or." Throughout this application, the term "about" is used to indicate that a value includes the inherent variation of error for the quantifying device, the method(s) being employed to determine the value, or the variation that exists among the study subjects. For example, but not by way of limitation, when the term "about" is utilized, the designated value may vary by plus or minus twelve percent, or eleven percent, or ten percent, or nine percent, or eight percent, or seven percent, or six percent, or five percent, or four percent, or three percent, or two percent, or one percent. The use of the term "at least one" will be understood to include one as well as any quantity more than one, including but not limited to, 1, 2, 3, 4, 5, 10, 15, 20, 30, 40, 50, 100, etc. The term "at least one" may extend up to 100 or 1000 or more depending on the term to which it is attached. In addition, the quantities of 100/1000 are not to be considered limiting as lower or higher limits may also produce satisfactory results. In addition, the use of the term "at least one of X, Y, and Z" will be understood to include X alone, Y alone, and Z alone, as well as any combination of X, Y, and Z. The use of ordinal number terminology (i.e., "first", "second", "third", "fourth", etc.) is solely for the purpose of differentiating between two or more items and, unless otherwise stated, is not meant to imply any sequence or order or importance to one item over another or any order of addition.

As used herein, the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. The terms "or combinations thereof" and "and/or combinations thereof" as used herein refer to all permutations and combinations of the listed items preceding the term. For example, "A, B, C, or combinations thereof" is intended to include at least one of: A, B, C, AB, AC, BC, or ABC and, if order is important in a particular context, also BA, CA, CB, CBA, BCA, ACB, BAC, or CAB. Continuing with this example, expressly included are combinations that contain repeats of one or more items or terms, such as BB, AAA, AAB, BBC, AAABCCCC, CBBAAA, CABABB, and so forth. The skilled artisan will understand that typically there is no limit on the number of items or terms in any combination, unless otherwise apparent from the context.

As used herein, the term "substantially" means that the subsequently described circumstance completely occurs or that the subsequently described circumstance occurs to a great extent or degree.

For purposes of the following detailed description, other than in any operating examples, or where otherwise indicated, numbers that express, for example, quantities of ingredients used in the specification and claims are to be understood as being modified in all instances by the term "about". The numerical parameters set forth in the specification and attached claims are approximations that may vary depending upon the desired properties to be obtained in carrying out the invention.

The term "alicyclic" refers to a cyclic group that is not aromatic. The group can be saturated or unsaturated, but it does not exhibit aromatic character.

The term "alkyl" refers to a saturated linear or branched hydrocarbon group of 1 to 50 carbons. It further includes both substituted and unsubstituted hydrocarbon groups. The term is further intended to include heteroalkyl groups.

The term "aprotic" refers to a class of solvents that lack an acidic hydrogen atom and are therefore incapable of acting as hydrogen donors. Common aprotic solvents include alkanes, carbon tetrachloride ($CCl_4$), benzene, dimethyl formamide (DMF), N-methyl-2-pyrrolidone (NMP), dimethylacetamide (DMAc), propylene glycol methyl ether acetate (PGMEA), anisole, cyclohexanone, benzyl benzoate, and many others.

The term "aromatic compound" refers to an organic compound comprising at least one unsaturated cyclic group having 4n+2 delocalized pi electrons. The term is intended to encompass both aromatic compounds having only carbon and hydrogen atoms, and heteroaromatic compounds wherein one or more of the carbon atoms within the cyclic group has been replaced by another atom, such as nitrogen, oxygen, sulfur, or the like.

The term "aryl" or "aryl group" refers to a moiety formed by removal of one or more hydrogen ("H") or deuterium ("D") from an aromatic compound. The aryl group may be a single ring (monocyclic) or have multiple rings (bicyclic, or more) fused together or linked covalently. A "carbocyclic aryl" has only carbon atoms in the aromatic ring(s). A "heteroaryl" has one or more heteroatoms in at least one aromatic ring.

The term "alkoxy" refers to the group —OR, where R is alkyl.

The term "aryloxy" refers to the group —OR, where R is aryl.

Unless otherwise indicated, all groups can be substituted or unsubstituted. An optionally substituted group, such as, but not limited to, alkyl or aryl, may be substituted with one or more substituents which may be the same or different. Suitable substituents include alkyl, aryl, nitro, cyano, —N(R')(R"), halo, hydroxy, carboxy, alkenyl, alkynyl, cycloalkyl, heteroaryl, alkoxy, aryloxy, heteroaryloxy, alkoxycarbonyl, perfluoroalkyl, perfluoroalkoxy, arylalkyl, silyl, siloxy, siloxane, thioalkoxy, —S(O)$_2$—, —C(=O)—N(R')(R"), (R')(R")N-alkyl, (R')(R")N-alkoxyalkyl, (R')(R") N-alkylaryloxyalkyl, —S(O)$_s$-aryl (where s=0-2) or —S(O)$_s$-heteroaryl (where s=0-2). Each R' and R" is independently an optionally substituted alkyl, cycloalkyl, or aryl group. R' and R", together with the nitrogen atom to which they are bound, can form a ring system in certain embodiments. Substituents may also be crosslinking groups.

The term "amine" refers to a compound that contains a basic nitrogen atom with a lone pair. The term "amino" refers to the functional group —$NH_2$, —NHR, or —$NR_2$, where R is the same or different at each occurrence and can be an alkyl group or an aryl group. The term "diamine" refers to a compound that contains two basic nitrogen atoms with associated lone pairs. The term "aromatic diamine" refers to an aromatic compound having two amino groups.

The term "aromatic diamine residue" refers to the moiety bonded to the two amino groups in an aromatic diamine. This is further illustrated below.

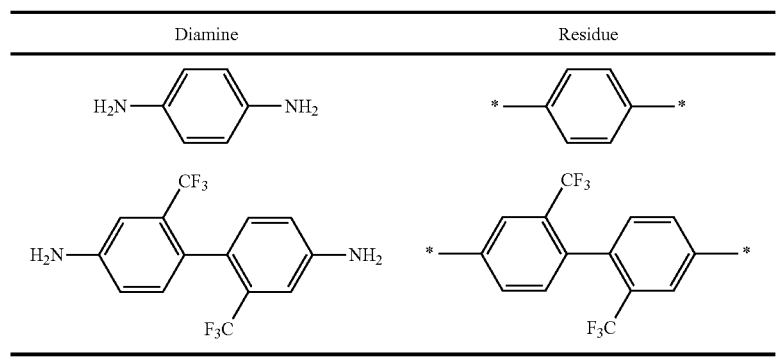

The term "diamine residue" refers to the moiety bonded to two amino groups where the moiety is aliphatic or aromatic.

The term "linear coefficient of thermal expansion (CTE or α)" refers to the parameter that defines the amount which a material expands or contracts as a function of temperature. It is expressed as the change in length per degree Celsius and is generally expressed in units of μm/m/° C. or ppm/° C.

$$\alpha = (\Delta L/L0)/\Delta T$$

CTE values may be measured via known methods during the first or second heating scan. The understanding of the relative expansion/contraction characteristics of materials can be an important consideration in the fabrication and/or reliability of electronic and display devices.

The term "electroactive" as it refers to a layer or a material, refers to a layer or material which electronically facilitates the operation of a device. Examples of electroactive materials include, but are not limited to, materials which conduct, inject, transport, or block a charge, where the charge can be either an electron or a hole, or materials which emit radiation or exhibit a change in concentration of electron-hole pairs when receiving radiation.

The term "fused," when applied to aromatic or alicyclic rings refers to an aromatic or alicyclic species that contains two or more joined rings that may share a single atom, two adjacent atoms, or 3 or more atoms.

The term "glass transition temperature (or $T_g$)" refers to the temperature at which a reversible change occurs in an amorphous polymer or in amorphous regions of a semi-crystalline polymer where the material changes suddenly from a hard, glassy, or brittle state to one that is flexible or elastomeric. Microscopically, the glass transition occurs when normally-coiled, motionless polymer chains become free to rotate and can move past each other. $T_g$'s may be measured using differential scanning calorimetry (DSC), thermo-mechanical analysis (TMA), dynamic-mechanical analysis (DMA), or other methods.

The term "haloalkyl" is refers to an alkyl group having one or more hydrogen atoms replaced by a halogen atom.

The term "haloalkoxy" refers to an alkoxy group having one or more hydrogen atoms replaced by a halogen atom.

The prefix "hetero" refers to a situation where one or more carbon atoms have been replaced with a different atom. In some embodiments, the heteroatom is O, N, S, or combinations thereof.

The term "high-boiling" refers to a boiling point greater than 130° C.

The term "imide" refers to a functional group containing two acyl groups bound to a central nitrogen, i.e., RCO—NR'—COR. The term "bis-imide" refers to the presence of two identical, but separated, imide groups in a single molecule, polymer, or other species.

The term "matrix" refers to a foundation on which one or more layers is deposited in the formation of, for example, an electronic device. Non-limiting examples include glass, silicon, and others.

The term "monomer" refers to a small molecule that chemically bonds during polymerization to one or more monomers of the same or different kind to form a polymer.

The term "nonpolar" refers to a molecule, solvent, or other species in which the distribution of electrons between covalently-bonded atoms is even and there is thus no net electrical charge across them. In some embodiments; nonpolar molecules, solvents, or other species are formed when constituent atoms have the same or similar electronegativities.

The term "organic electronic device" or sometimes "electronic device" refers to a device including one or more organic semiconductor layers or materials.

The term "polar" refers to a molecule, solvent, or other species in which the distribution of electrons between covalently-bonded atoms is not even. Such species therefore exhibit a large dipole moment which may result from bonds between atoms characterized by significantly-different electronegativities.

The term "polyimide" refers to condensation polymers resulting from the reaction of one or more bifunctional carboxylic acid components with one or more primary diamines or diisocyanates. Polyimides contain the imide structure —CO—NR—CO— as a linear or heterocyclic unit along the main chain of the polymer backbone.

The term "polymer" refers to a large molecule comprising one or more types of monomer residues (repeating units) connected by covalent chemical bonds. By this definition, a polymer encompasses compounds wherein the number of monomer units may range from very few, which more commonly may be called as oligomers, to very many. Non-limiting examples of polymers include homopolymers and non-homopolymers such as copolymers, terpolymers, tetrapolymers and the higher analogues.

The term "polyarylene" refers to a class of polymers that contain benzenoid aromatic components directly joined to one another by carbon-carbon bonds along the main chain of the polymer backbone.

The term "protic" refers to a class of solvents that contain an acidic hydrogen atom and are therefore capable of acting as hydrogen donors. Common protic solvents include formic acid, n-butanol, isopropanol, ethanol, methanol, acetic acid, water, propylene glycol methyl ether (PGME), propylene glycol methyl ether acetate (PGMEA), and others. Protic solvents can be used individually or in various combinations.

The term "satisfactory," when regarding a materials property or characteristic, is intended to mean that the property or characteristic fulfills all requirements/demands for the material in-use. For example, a 30:1 dilution polymer solution that exhibits a shock test rating of 4.5 at 12 weight % may be viewed as a non-limiting example of a "satisfactory" property in the context of the polymers disclosed herein.

The term "shock test" refers to a method to assess polymer solubility wherein polymers are formulated in an appropriate solvent system in a specified concentration, optionally filtered, diluted, and subject to a test solvent system of interest. The polymer/solvent systems are rolled to mix, and solubility ratings are assessed by visual inspection for extent of mixing and amount of precipitation. In some embodiments, an appropriate solubility rating scale is that which is disclosed in detail herein.

The term "solubility" refers to the maximum amount of solute that can be dissolved in a solvent at a given temperature. In some embodiments, solubility may be measured or assessed by any number of qualitative or quantitative methods.

The term "substrate" refers to a base material that can be either rigid or flexible and may include one or more layers of one or more materials, which can include, but are not limited to, glass, polymer, metal or ceramic materials or combinations thereof. The substrate may or may not include electronic components, circuits, or conductive members.

The term "tetracarboxylic acid component" refers to any one or more of the following: a tetracarboxylic acid, a tetracarboxylic acid monoanhydride, a tetracarboxylic acid dianhydride, a tetracarboxylic acid monoester, and a tetracarboxylic acid diester.

The term "tetracarboxylic acid component residue" refers to the moiety bonded to the four carboxy groups in a tetracarboxylic acid component. This is further illustrated below.

In a structure where a substituent bond passes through one or more rings as shown below,

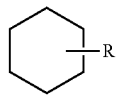 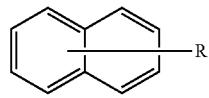

it is meant that the substituent R may be bonded at any available position on the one or more rings.

The phrase "adjacent to," when used to refer to layers in a device, does not necessarily mean that one layer is immediately next to another layer. On the other hand, the phrase "adjacent R groups," is used to refer to R groups that are next to each other in a chemical formula (i.e., R groups that are on atoms joined by a bond). Exemplary adjacent R groups are shown below:

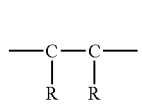 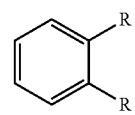

All percentages, ratios, and proportions used herein are based on weight unless otherwise specified.

The present disclosure is directed to a bis-imide compound comprising two or more aryl moieties substituted with ethynyl moieties and the two or more aryl moieties each having one or more polar substituents. The aryl moieties are selected from any number of groups that include 6 to 60 ring carbon atoms and may also include heteroatoms. The ethynyl moieties are any containing a carbon-carbon triple bond.

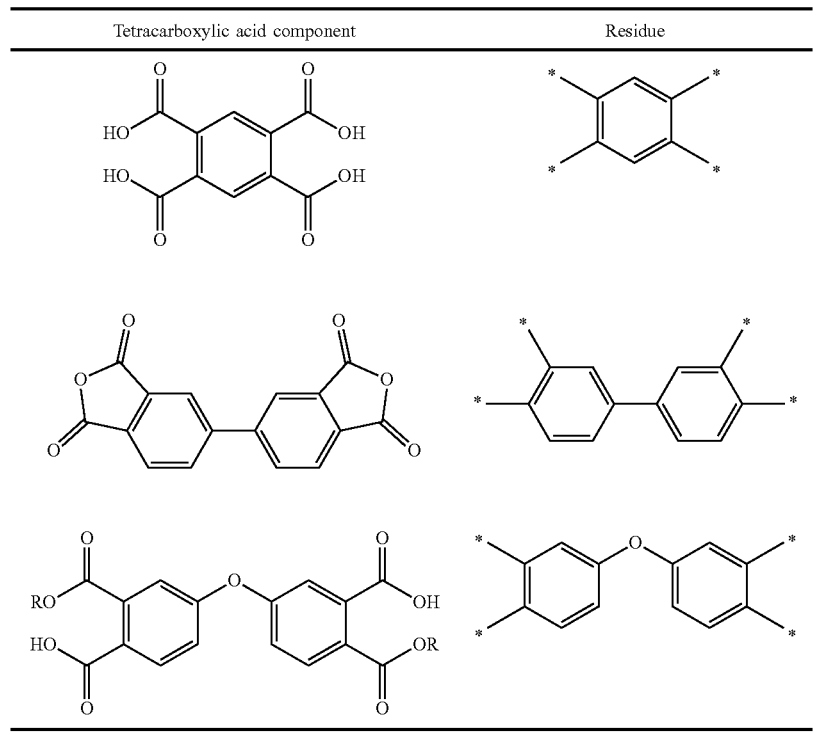

Polar substituents are any in which the distribution of electrons between covalently-bonded atoms is not even as disclosed herein.

In one non-limiting embodiment, the bis-imide compound of the present disclosure can be represented by Formula 1a:

Formula 1a

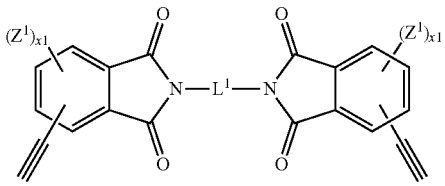

where $L^1$ is a divalent linking group substituted with $(Z^2)_y$; $Z^1$ and $Z^2$ are polar groups; x1 and y are the same or different and are integers from 0 to 4, such that x1+y is an integer from 2 to 6.

In one non-limiting embodiment; $L^1$ is a divalent aromatic linking group that can be selected from the group consisting of hydrocarbon aryl groups, heteroaryl groups, and substituted derivatives thereof. In another non-limiting embodiment; $L^1$ is a divalent linking group that can be an unsubstituted hydrocarbon aryl or a hydrocarbon aryl having 6-30 ring carbons or a hydrocarbon aryl having 6-18 ring carbons. In another non-limiting embodiment; $L^1$ is selected from the group consisting of phenyl, biphenyl, terphenyl, naphthyl and substituted derivatives thereof.

In another non-limiting embodiment; $L^1$ is selected from the group consisting of heteroaryl, where the heteroaryl has at least one ring atom which is selected from the group consisting of O, N, and S. In one non-limiting embodiment; $L^1$ is an O-heteroaryl having at least one ring atom that is O. In another non-limiting embodiment; the O-heteroaryl is derived from a compound selected from the group consisting of furan, benzofuran, isobenzofuran, dibenzofuran, and substituted derivatives thereof. In one non-limiting embodiment; L' is an S-heteroaryl having at least one ring atom which is S. In another non-limiting embodiment; the S-heteroaryl is derived from a compound selected from the group consisting of thiophene, benzothiophene, isobenzothiophene, dibenzothiophene, and substituted derivatives thereof.

In another non-limiting embodiment of Formula 1a, $L^1$ has Formula 2a:

Formula 2a

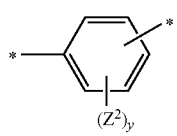

where $Z^2$ and y are as defined elsewhere herein; and * denotes the points of attachment to the imide nitrogens of Formula 1a.

In another non-limiting embodiment of Formula 1a, $L^1$ has Formula 2b:

Formula 2b

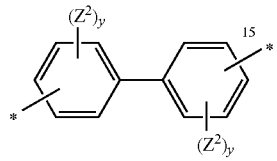

where $Z^2$ and y are as defined elsewhere herein; and * denotes the points of attachment to the imide nitrogens of Formula 1a.

In another non-limiting embodiment of Formula 1a, $L^1$ has Formula 2c or formula 2d:

Formula 2c

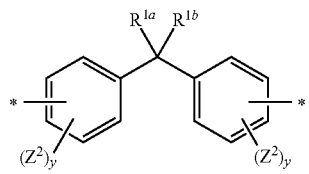

Formula 2d

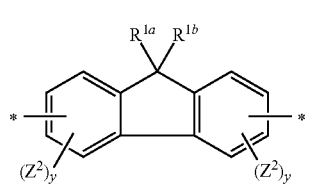

where $R^{1a}$, and $R^{1b}$ are the same or different and can be selected from the group consisting of H, halogen, $C_{1-30}$ alkyl, $C_{1-C30}$ heteroalkyl, $C_{2-30}$ alkenyl, $C_{7-30}$ aralkyl, $C_{6-30}$ aryl, and $C_{4-30}$ heteroaryl; and $Z^2$, y, and * are as defined elsewhere herein.

In one non-limiting embodiment of Formula 2c and Formula 2d; $R^{1a}$ and $R^{1b}$ are F or $CF_3$.

In another non-limiting embodiment; $L^1$ is an alicyclic ring selected from the group consisting of cyclopropane, cyclobutane, cyclopentane, cyclohexane, cycloheptane, cyclooctane, bicycloundecane, decalin, housane, and the like and similar species.

In another non-limiting embodiment of Formula 1a; $L^1$ can be selected from the group consisting of the following species:

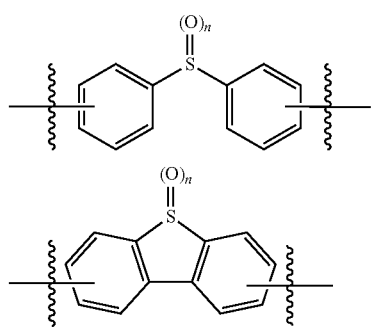

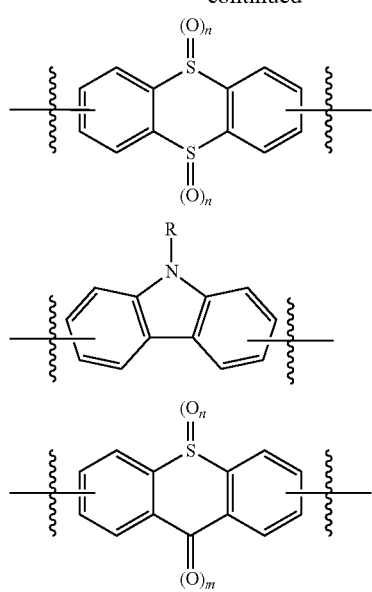

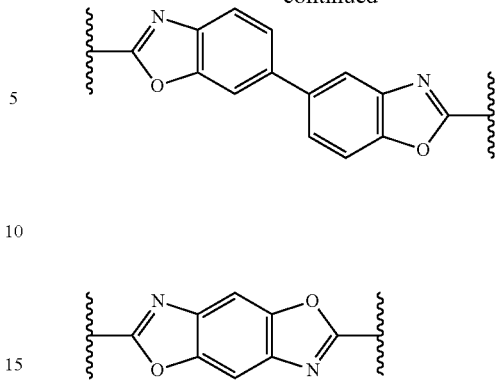

where n is the same or different at each occurrence and is 0, 1, or 2; and m is 0 or 1.

In another non-limiting embodiment of Formula 1a; Formula 1a is given by Formula 1a':

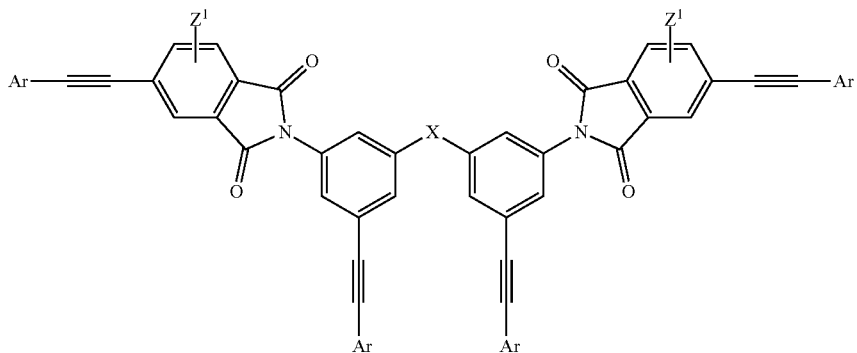

Formula 1a'

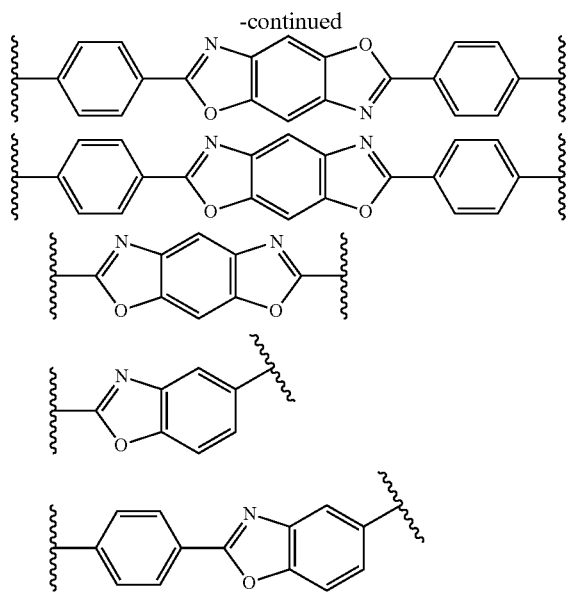

where Ar groups are the same or different at each occurrence and are selected from the group consisting of $C_6$-$C_{30}$ aryl groups; $Z^1$ is the same or different at each occurrence and is a polar group; X is selected from the group consisting of S, O, SO, $SO_2$, and NR; and R is selected from the group consisting of H, halogen, $C_{1-30}$ alkyl, $C_{1\text{-}C30}$ heteroalkyl, $C_{2-30}$ alkenyl, $C_{7-30}$ aralkyl, $C_{6-30}$ aryl, and $C_{4-30}$ heteroaryl.

In some non-limiting embodiments of Formula 1a'; Ar groups are the same at each occurrence or different at each occurrence or selected from the group consisting of $C_5$-$C_{30}$ heteroaryl groups. In some non-limiting embodiments of Formula 1a'; Ar groups are the same or different at each occurrence and are selected from the group consisting of $C_6$-$C_{18}$ aryl groups. In some non-limiting embodiments of Formula 1a'; Ar groups are the same or different at each occurrence and are selected from the group consisting of benzyl, napththyl, phenanthryl, and terphenyl. In some non-limiting embodiments of Formula 1a; X is S or 0 or SO or $SO_2$ or NR. In some non-limiting embodiments of Formula 1a; R is H or halogen or $C_{1-30}$ alkyl or $C_{1-30}$ heteroalkyl or $C_{2-30}$ alkenyl or $C_{7-30}$ aralkyl or $C_{6-30}$ aryl or $C_{4-30}$ heteroaryl.

In some non-limiting embodiments of Formula 1a or Formula 1a'; polar groups $Z^1$ and $Z^2$ are the same at each occurrence. In other non-limiting embodiments of Formula 1a or Formula 1a'; polar groups $Z^1$ and $Z^2$ are different at each occurrence. In some non-limiting embodiments of Formula 1a or Formula 1a'; polar groups $Z^1$ and $Z^2$ can be selected from the group consisting of OH, $CO_2H$, $CO_2R$, OR, $CX_3$, F, Cl, Br, SH, $CONH_2$, CONHR, $CONR_2$, and SR; where R is as disclosed elsewhere herein and X is a halogen.

In other non-limiting embodiment of Formula 1a or Formula 1a'; polar groups $Z^1$ and $Z^2$ are selected from the group consisting of $NR_2$,

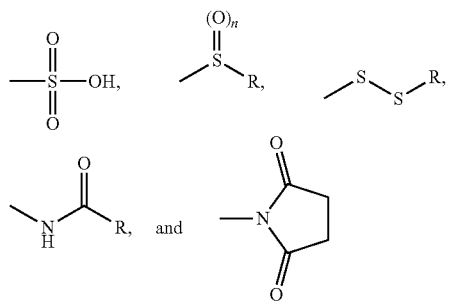

where R is as disclosed elsewhere herein and n=1 or n=2.

In some non-limiting embodiments of Formula 1a; x1=0 or x1=1 or x1=2 or x1=3 or x1=4; y=0 or y=1 or y=2 or y=3 or y=4; x1+y=2 or x1+y=3 or x1+y=4 or x1+y=5 or x1+y=6.

Any of the above embodiments of Formula 1a and Formula 1a' can be combined with one or more of the other embodiments, so long as they are not mutually exclusive. For example, the embodiment of Formula 1a in which $L^1$ is a hydrocarbon aryl group can be combined with the embodiment of Formula 1a in which $Z^1$ is OH. The same is true for other non-mutually-exclusive embodiments discussed above. The skilled person would understand which embodiments were mutually exclusive and would thus readily be able to determine the combinations of embodiments that are contemplated by the present application.

Some non-limiting examples of compounds having Formula 1a are:

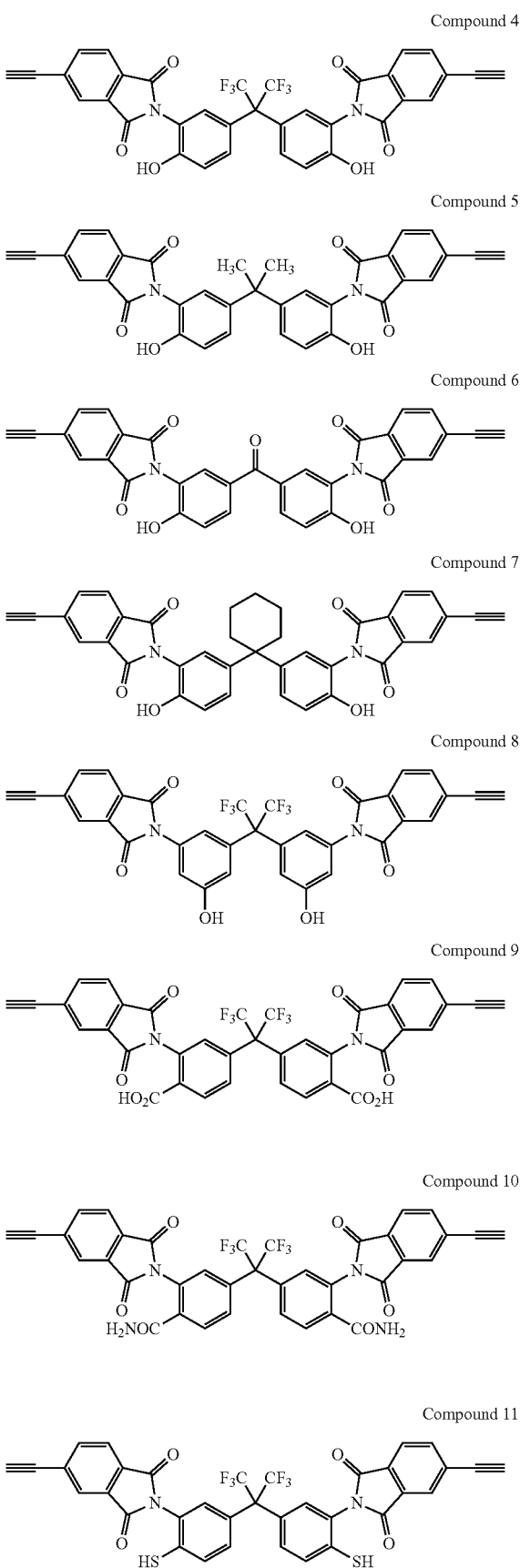

Compound 12

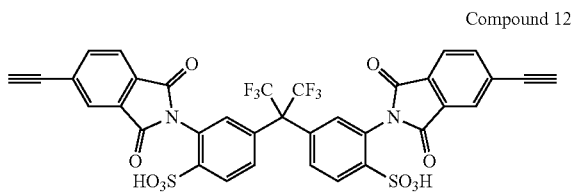

In one non-limiting embodiment, the bis-imide compound of the present disclosure can be represented by Formula 1b:

Formula 1b

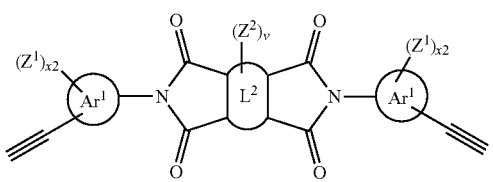

where $L^2$ is a fused aromatic or alicyclic ring; $Z^1$ and $Z^2$ are polar groups; $Ar^1$ is the same or different at each occurrence and is a $C_6$-$C_{30}$ aryl group; x2 is an integer from 0 to 4; v is an integer from 0 to 2, provided that v is 0 when $L^2$ is an alicyclic ring; and x2+v is an integer from 2 to 4.

In one non-limiting embodiment of Formula 1b, $L^2$ is a fused aromatic ring selected from the group consisting of benzene, naphthalene, phenanthrene, phenalene, tetracene, chrysene, triphenylene, pyrene, pentacene, and the like and including species with more fused rings. In another non-limiting embodiment, $L^2$ is a phenyl group. In another non-limiting embodiment of Formula 1b, $L^2$ is a naphthyl group. In another non-limiting embodiment of Formula 1b, $L^2$ is a fused aromatic ring structure containing one or more heteroatoms. In another non-limiting embodiment of Formula 1b; $L^2$ can be selected from the group consisting of the following species:

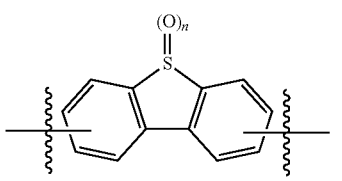

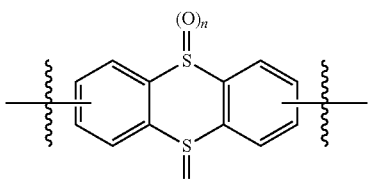

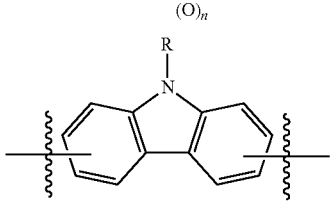

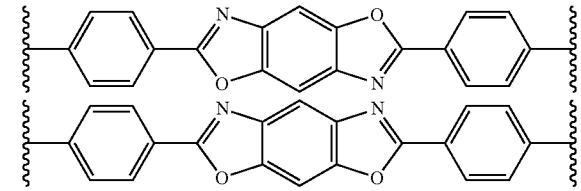

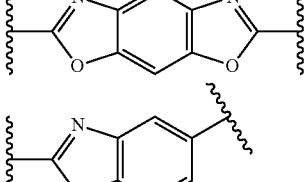

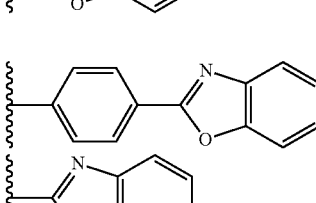

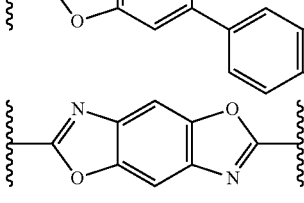

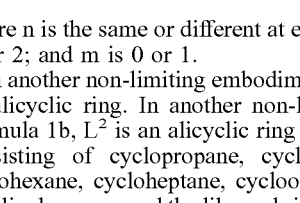

where n is the same or different at each occurrence and is 0, 1, or 2; and m is 0 or 1.

In another non-limiting embodiment of Formula 1b, $L^2$ is an alicyclic ring. In another non-limiting embodiment of Formula 1b, $L^2$ is an alicyclic ring selected from the group consisting of cyclopropane, cyclobutane, cyclopentane, cyclohexane, cycloheptane, cyclooctane, bicycloundecane, decalin, housane, and the like and similar species. In another non-limiting embodiment of Formula 1b, $L^2$ is selected from the group consisting of cyclobutane, cyclopentane, and cyclohexane. In another non-limiting embodiment of Formula 1b, $L^2$ is selected from the group consisting of a 4- to 6-membered alicyclic ring, a benzene ring, and a naphthalene ring. In another non-limiting embodiment of Formula 1b, $L^2$ contains one or more heteroatoms. In another non-limiting embodiment of Formula 1b, $L^2$ contains heteroatoms selected from the group consisting of N, O and S.

In another non-limiting embodiment of Formula 1b, $L^2$ is:

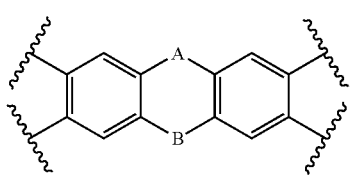

where A and B are the same or different at each occurrence and are selected from the group consisting of $CH_2$, $CF_2$, $C(CH_3)_2$, $C(CH_3)(CF_3)$, $C(CF_3)_2$, $C(O)$, O, S, SO, $SO_2$, and fluorenyl.

In another non-limiting embodiment of Formula 1b; Formula 1b is given by Formula 1b':

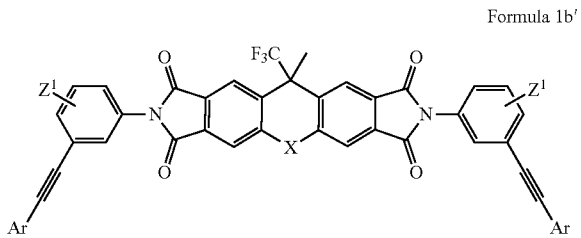

Formula 1b' where Ar groups are the same or different at each occurrence and are selected from the group consisting of $C_6$-$C_{30}$ aryl groups; $Z^1$ is a polar group; X is selected from the group consisting of S, O, SO, $SO_2$, and NR; and R is selected from the group consisting of H, halogen, $C_{1-30}$ alkyl, $C_1$-$C_{30}$ heteroalkyl, $C_{2-30}$ alkenyl, $C_{7-30}$ aralkyl, $C_{6-30}$ aryl, and $C_{4-30}$ heteroaryl.

Non-limiting, specific embodiments for Ar, $Z^1$, and X in Formula 1b' are the same as those identified in the context of Formula 1a' disclosed herein.

In one non-limiting embodiment of Formula 1b, $Ar^1$ is the same or different at each occurrence and is selected from the group consisting of $C_6$-$C_{30}$ aryl groups. In another non-limiting embodiment of Formula 1b, $Ar^1$ is the same or different at each occurrence and is selected from the group consisting of benzyl, naphthyl, phenanthryl, triphenyl, and the like and including species with more fused rings. In another non-limiting embodiment of Formula 1b, AO is the same or different at each occurrence and is selected from the group consisting of $C_5$-$C_{30}$ heteroaryl groups. In another non-limiting embodiment of Formula 1b, $Ar^1$ is the same or different at each occurrence and contains N, O, or S as a heteroatom.

In some non-limiting embodiments of Formula 1b'; X is S or 0 or SO or $SO_2$ or NR. In some non-limiting embodiments of Formula 1b'; R is H or halogen or $C_{1-30}$ alkyl or $C_{1-30}$ heteroalkyl or $C_{2-30}$ alkenyl or $C_{7-30}$ aralkyl or $C_{6-30}$ aryl or $C_{4-30}$ heteroaryl.

In some non-limiting embodiments of Formula 1b or Formula 1b'; polar groups $Z^1$ and $Z^2$ are the same at each occurrence. In other non-limiting embodiments of Formula 1b or Formula 1b'; polar groups $Z^1$ and $Z^2$ are different at each occurrence. In some non-limiting embodiments of Formula 1b or Formula 1b'; polar groups $Z^1$ and $Z^2$ can be selected from the group consisting of OH, $CO_2H$, $CO_2R$, OR, $CX_3$, F, Cl, Br, SH, $CONH_2$, CONHR, $CONR_2$, and SR; where R is as disclosed elsewhere herein and X is a halogen.

In other non-limiting embodiment of Formula 1b or Formula 1b'; polar groups $Z^1$ and $Z^2$ are selected from the group consisting of $NR_2$,

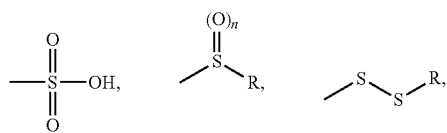

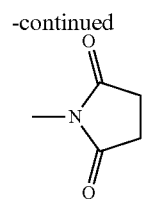

where R is as disclosed elsewhere herein and n=1 or n=2.

In some non-limiting embodiments of Formula 1b; x2=0 or x2=1 or x2=2 or x2=3 or x2=4; v=0 when $L^2$ is a fused aromatic ring or v=0 when $L^2$ is a fused alicyclic ring or v=1 or v=2; x2+v=2 or x2+v=3 or x2+v=4.

Any of the above embodiments of Formula 1b or Formula 1b' can be combined with one or more of the other embodiments, so long as they are not mutually exclusive. For example, the embodiment of Formula 1b in which $L^2$ is a fused aromatic ring can be combined with the embodiment of Formula 1b in which $Z^1$ is $CF_3$. The same is true for other non-mutually-exclusive embodiments discussed above. The skilled person would understand which embodiments were mutually exclusive and would thus readily be able to determine the combinations of embodiments that are contemplated by the present application.

Some non-limiting examples of compounds having Formula 1b are:

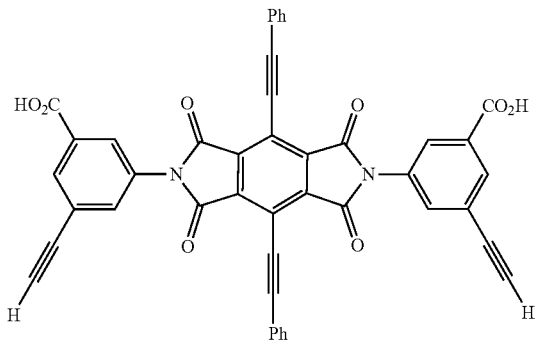

Compound 13

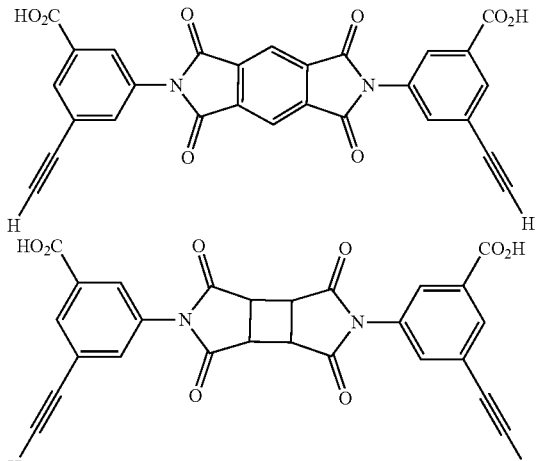

Compound 14

In one non-limiting embodiment, the bis-imide compound of the present disclosure can be represented by Formula 1c:

Formula 1c

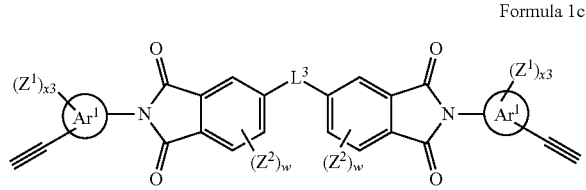

where $L^3$ is a divalent linking group; all embodiments of $Ar^1$, $Z^1$, and $Z^2$ disclosed herein for Formula 1a and Formula 1b apply equally well to $Ar^1$, $Z^1$, and $Z^2$ in Formula 1c; x3 is an integer from 0 to 4; and w is an integer from 0 to 3, such that x3+w is an integer from 2 to 6.

In one non-limiting embodiment of Formula 1c; $L^3$ is selected from the group consisting of a single covalent bond, an alkyl group, O, S, C(O), C(S), S(O), $SO_2$, $CF_2$, and $C(CF_3)_2$.

In some non-limiting embodiments of Formula 1c; x3=0 or x3=1 or x3=2 or x3=3 or x3=4; w=0 or w=1 or w=2 or w=3; x3+w=2 or x3+w=3 or x3+w=4 or x3+w=5 or x3+w=6.

Any of the above embodiments of Formula 1c can be combined with one or more of the other embodiments, so long as they are not mutually exclusive. For example, the embodiment in which $L^3$ is —$C(CF_3)_2$ can be combined with the embodiment in which x3 is 2. The same is true for other non-mutually-exclusive embodiments discussed above. The skilled person would understand which embodiments were mutually exclusive and would thus readily be able to determine the combinations of embodiments that are contemplated by the present application.

Some non-limiting examples of compounds having Formula 1c are:

Compound 16

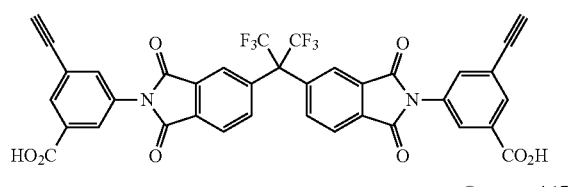

Compound 17

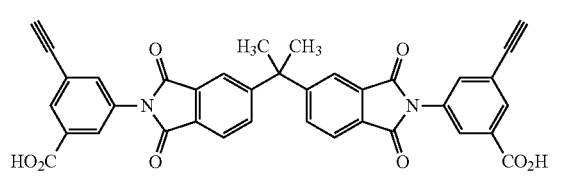

Compound 18

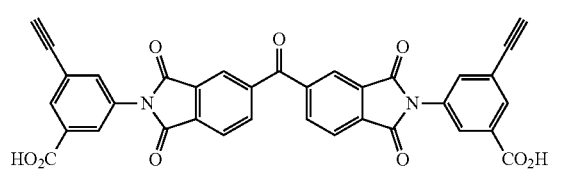

Compound 19

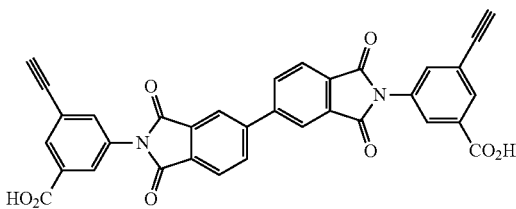

Compound 20

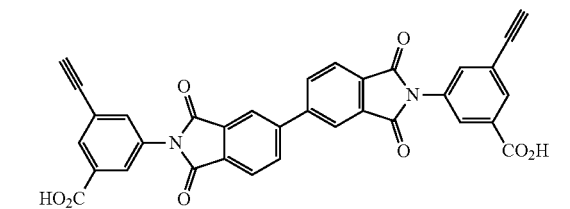

Compound 21

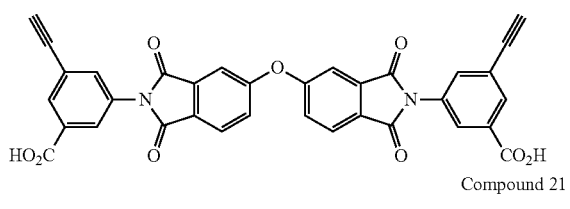

Compound 22

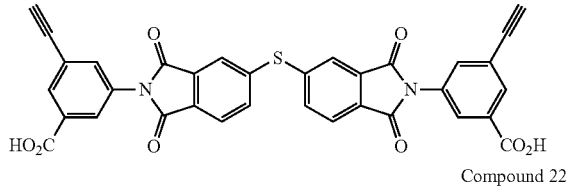

Compound 23

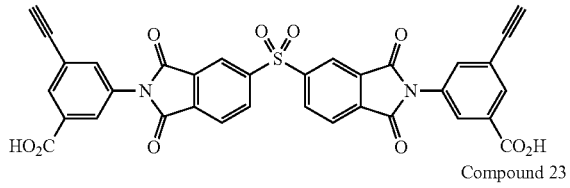

Compound 24

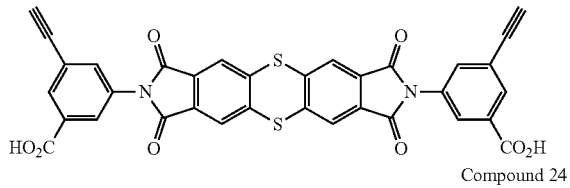

The present disclosure is further directed to a polymer composition comprising a copolymer polymerized from a monomer mixture of (a) one or more first monomers comprising a bis-imide compound comprising two or more aryl moieties substituted with ethynyl moieties and the two or more aryl moieties each having one or more polar substituents; and (b) one or more second monomers comprising two or more cyclopentadienone moieties. The one or more first monomers comprising a bis-imide compound comprising two or more aryl moieties substituted with ethynyl moieties and the two or more aryl moieties each having one or more polar substituents is selected from the group consisting of a compound having Formula 1a, a compound having Formula 1b, and a compound having Formula 1c as disclosed herein.

The one or more second monomers comprising two or more cyclopentadienone moieties of the polymer composition can be represented by Formula 3:

Formula 3

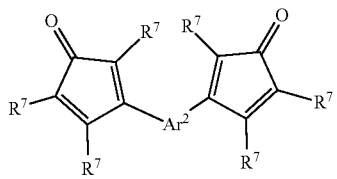

Where $R^7$ is the same or different at each occurrence and is selected from the group consisting of H, substituted or unsubstituted $C_{1-6}$ alkyl, substituted or unsubstituted $C_{6-20}$ aryl, and substituted or unsubstituted $C_{4-20}$ heteroaryl; and $Ar^2$ is a substituted or unsubstituted $C_{6-20}$ aryl group.

In one non-limiting embodiment of Formula 3; $R^7$ can be the same at each occurrence or different at each occurrence. In another non-limiting embodiment; $R^7$ can be H or unsubstituted $C_{1-6}$ alkyl or substituted $C_{1-6}$ alkyl or unsubstituted $C_{6-30}$ aryl or substituted $C_{6-30}$ aryl or unsubstituted $C_{5-30}$ heteroaryl or substituted $C_{5-30}$ heteroaryl.

In one non-limiting embodiment of Formula 3; $Ar^2$ is a substituted or unsubstituted $C_{6-20}$ aryl group. A wide variety of aromatic moieties is suitable for use as $Ar^2$. Many of these are disclosed in U.S. Pat. No. 5,965,679.

In one non-limiting embodiment of Formula 3; $Ar^2$ has Formula 4:

Formula 4

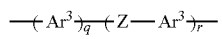

where q is an integer from 1 to 3; r is an integer from 0 to 2; $Ar^3$ is the same or different at each occurrence and is selected from the group consisting of Formula 5 and Formula 6:

Formula 5

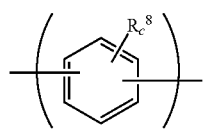

Formula 6

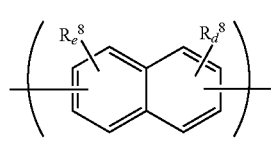

where $R^8$ is the same or different at each occurrence and is selected from the group consisting of halogen, substituted or unsubstituted $C_{1-6}$ alkyl, aryl, and aryloxy; c is an integer from 0 to 4; d and e are the same or different at each occurrence and are each an integer from 0 to 3; Z is the same or different at each occurrence and selected from the group consisting of a single covalent bond, an alkyl group, O, C(O), C(S), $CF_2$, and $C(CF_3)_2$.

In another non-limiting embodiment of Formula 4; Z is the same or different at each occurrence and is selected from the group consisting of $CH_2$, $CF_2$, $C(CH_3)_2$, $C(CF_3)_2$, fluorenyl, O, S, SO, $SO_2$, $NR^9$, $PR^9$, $P(=O)R^9$, $C(=O)$, $CR^{10}R^{11}$, $SiR^{10}R^{11}$,

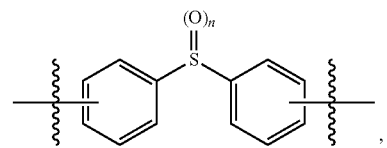

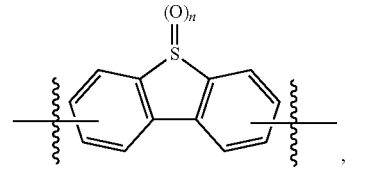

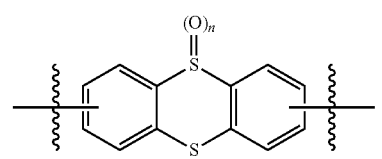

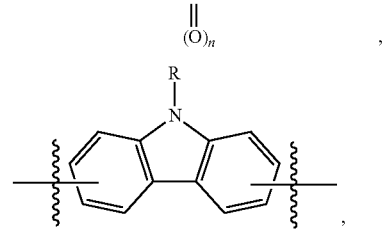

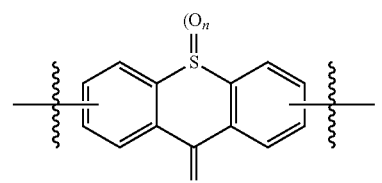

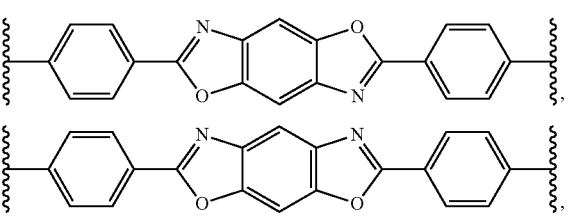

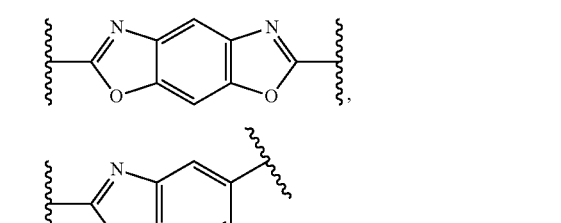

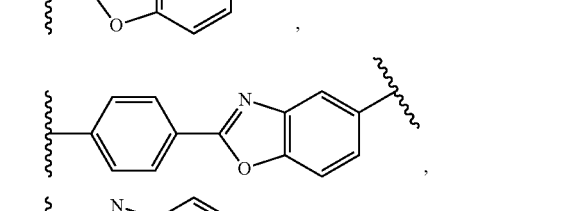

and

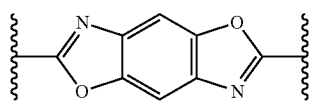

where R is defined as elsewhere herein; and $R^9$, $R^{10}$, and $R^{11}$ are the same or different and are selected from the group consisting of H, substituted or unsubstituted $C_{1-4}$ alkyl, and aryl.

In some non-limiting embodiments of Formula 5 and Formula 6, one or more of $R^8$ is selected from the group consisting of halogen, $C_{1-4}$ haloalkyl, $C_{1-4}$ haloalkoxy, phenyl, phenoxy, fluoro, $C_{1-4}$ alkyl, $C_{1-4}$ fluoroalkyl, and $C_{1-4}$ fluoroalkoxy.

In some non-limiting embodiments of Formula 5 and Formula 6, c=0 or c=1 or c=2 or c=3.

In some non-limiting embodiments of Formula 5 and Formula 6, each of d and e is independently 0 or 1 or 2.

In another non-limiting embodiment of Formula 5 and Formula 6, d+e is 0 or 1 or 2 or 3 or 4.

In some non-limiting embodiments of Formula 4, q=1 or q=2.

In some non-limiting embodiments of Formula 4, r=0 or r=1.

In another non-limiting embodiment of Formula 4, each Z is independently selected from the group consisting of O, S, $NR^9$, C(O), $C^{10}R^{11}$ and $SiR^{10}R^{11}$, where each of $R^9$, $R^{10}$, and $R^{11}$ is independently H or $C_{1-4}$ alkyl or $C_{1-2}$ fluoroalkyl or phenyl.

Some non-limiting examples of the one or more first monomers comprising a bis-imide compound comprising two or more aryl moieties substituted with ethynyl moieties and the two or more aryl moieties each having one or more polar substituents are selected from the group consisting of a compound having Formula 1a, a compound having Formula 1b, and a compound having Formula 1c as disclosed herein.

Some non-limiting examples of the one or more second monomers comprising two or more cyclopentadienone moieties are:

Compound M2-1

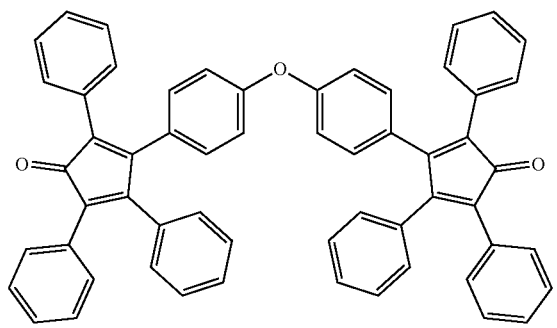

Compound M2-2

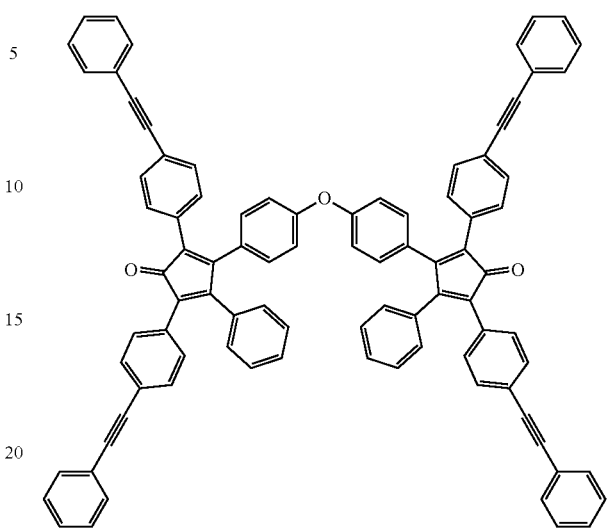

Compound M2-3

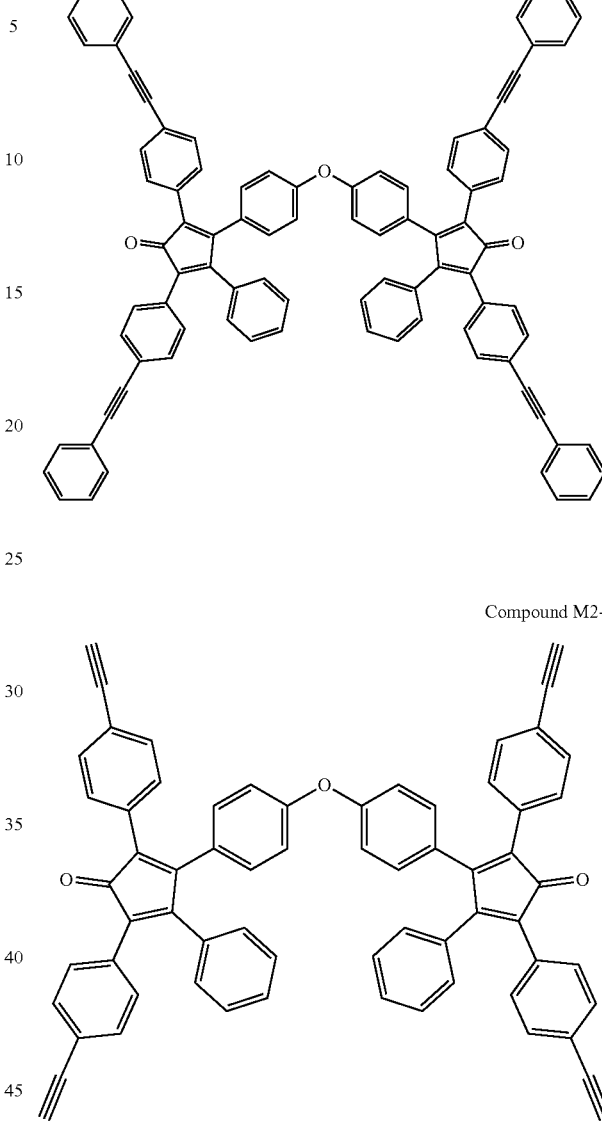

Compound M2-4

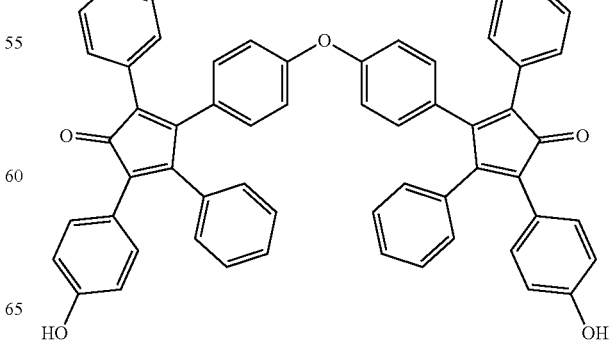

Compound M2-5

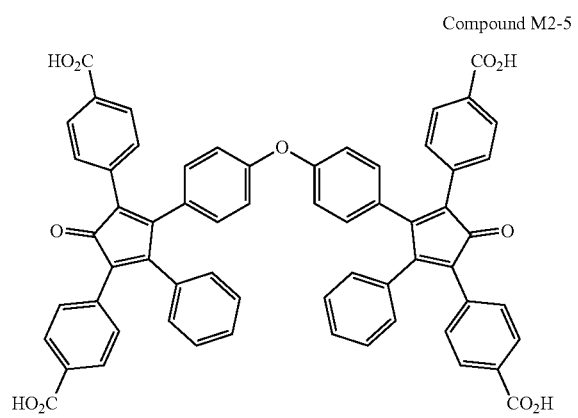

Compound M2-6

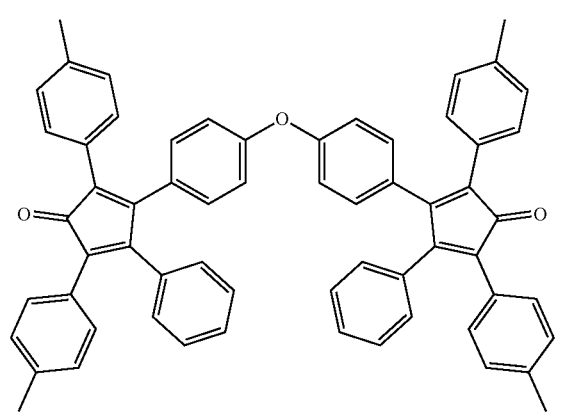

Compound M2-7

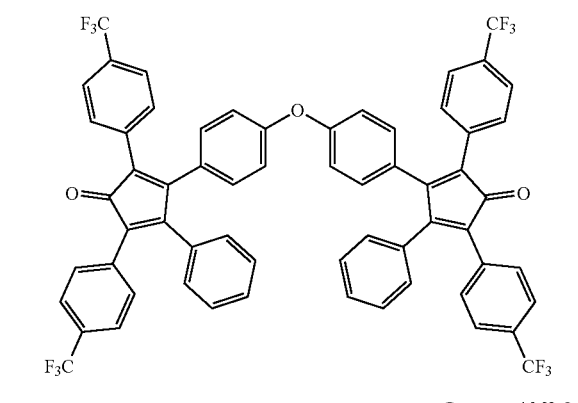

Compound M2-8

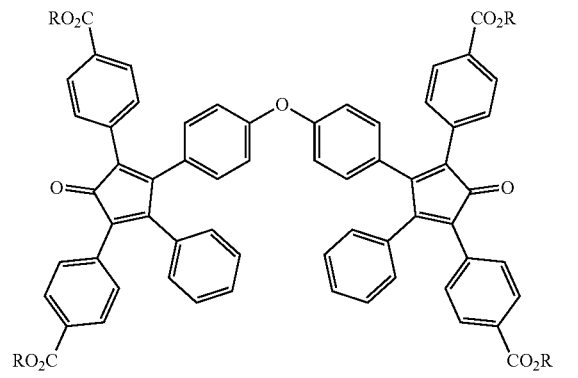

Compound M2-9

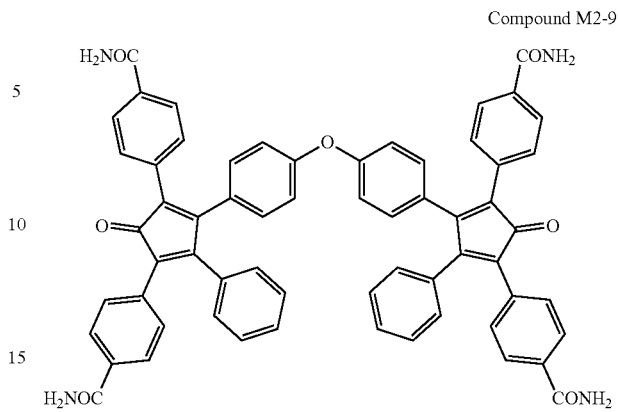

Compound M2-10

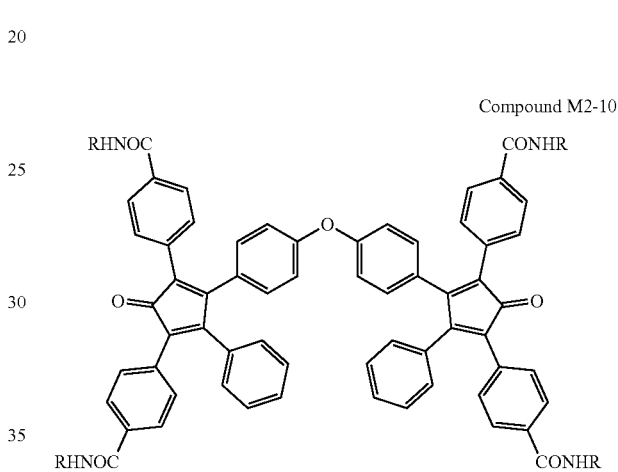

Compound M2-11

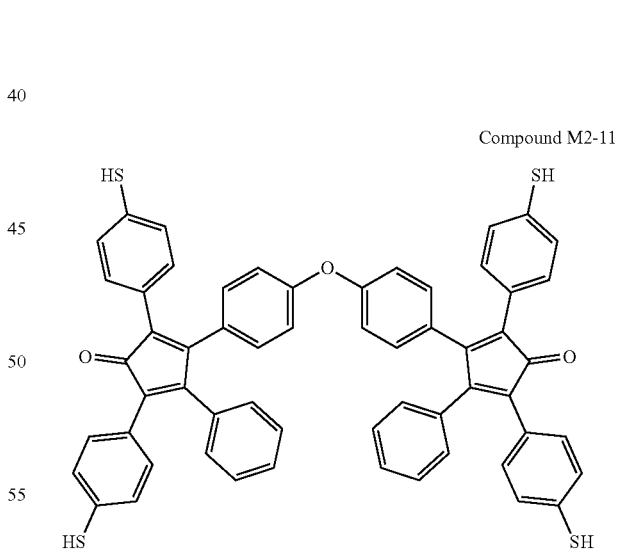

Some non-limiting examples of the polymer composition comprising a copolymer polymerized from a monomer mixture of (a) one or more first monomers comprising a bis-imide compound comprising two or more aryl moieties substituted with ethynyl moieties and the two or more aryl moieties each having one or more polar substituents; and (b) one or more second monomers comprising two or more cyclopentadienone moieties are:

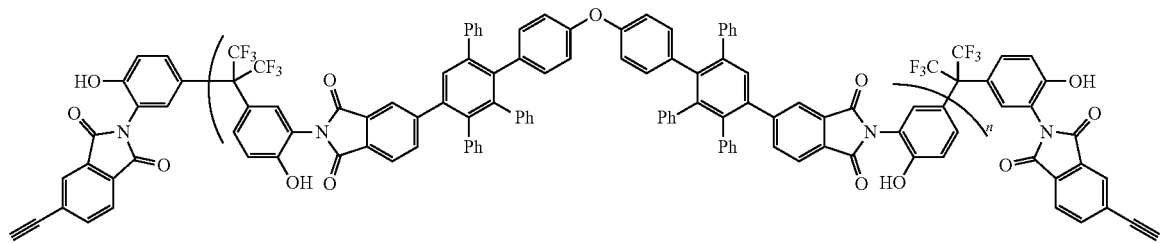
Polymer 1
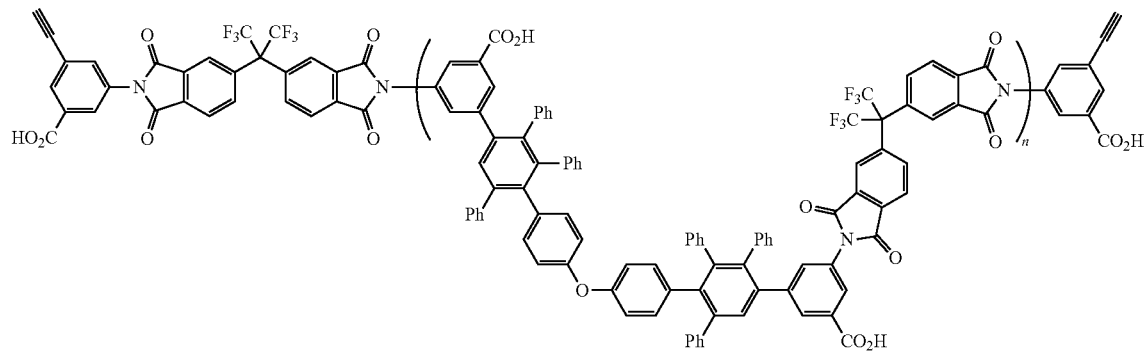
Polymer 2
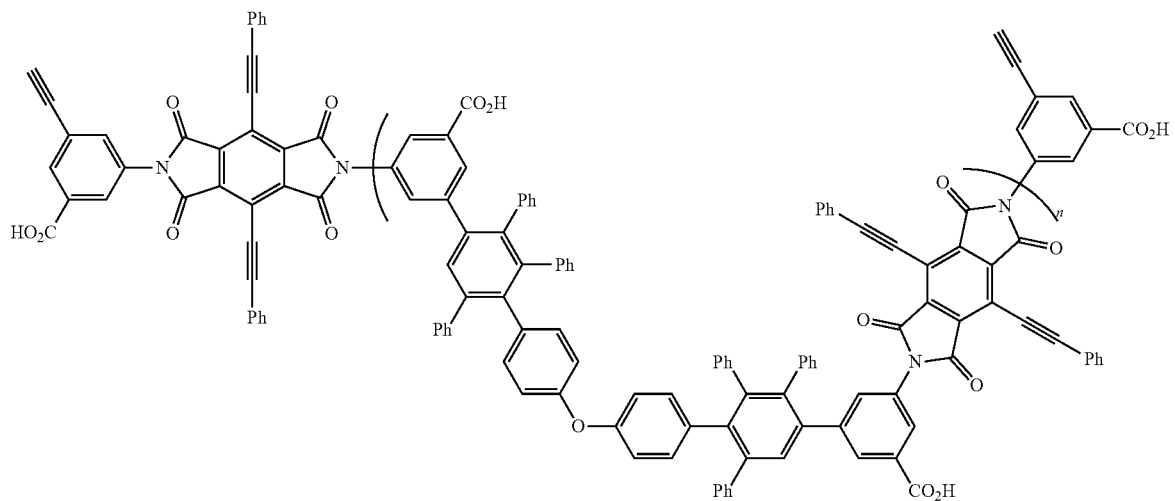
Polymer 3

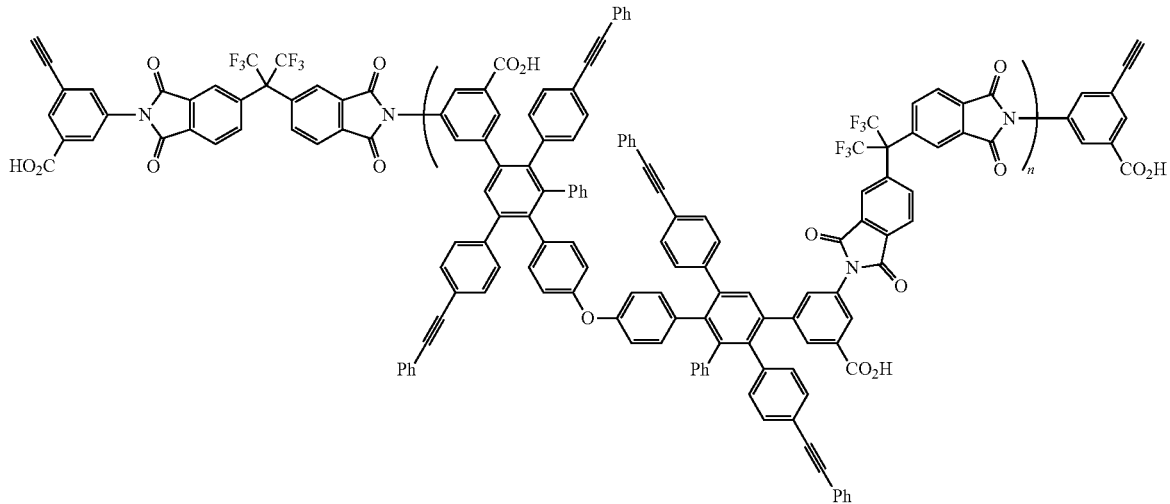

Polymer 4

The present disclosure is further directed to polymer compositions comprising ter- and higher-polymers polymerized from monomer mixtures of (a) two or more first monomers each comprising a bis-imide compound comprising two or more aryl moieties substituted with ethynyl moieties and the two or more aryl moieties each having one or more polar substituents; and (b) one or more second monomers comprising two or more cyclopentadienone moieties. The two or more first monomers each comprising a bis-imide compound comprising two or more aryl moieties substituted with ethynyl moieties and the two or more aryl moieties each having one or more polar substituents is selected from the group consisting of a compound having Formula 1a, a compound having Formula 1b, and a compound having Formula 1c as disclosed herein.

Such polymer compositions have embodiments that offer the potential for the production of new materials that offer additional flexibility in terms of final-polymer properties that can be optimized for electronics and displays applications. Materials disclosed herein, produced via the judicious choice of monomeric materials and respective relative amounts, can be adjusted in terms of their processability, thermal stability, CTE, solubility, and other properties as disclosed herein. A non-limiting example of a polymer compositions comprising ter- and higher-polymers polymerized from monomer mixtures of (a) two or more first monomers each comprising a bis-imide compound comprising two or more aryl moieties substituted with ethynyl moieties and the two or more aryl moieties each having one or more polar substituents; and (b) one or more second monomers comprising two or more cyclopentadienone moieties is:

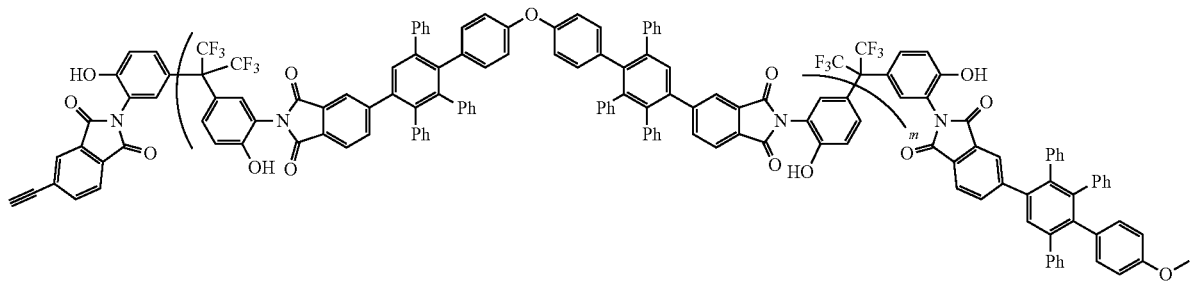

Polymer 5

-continued

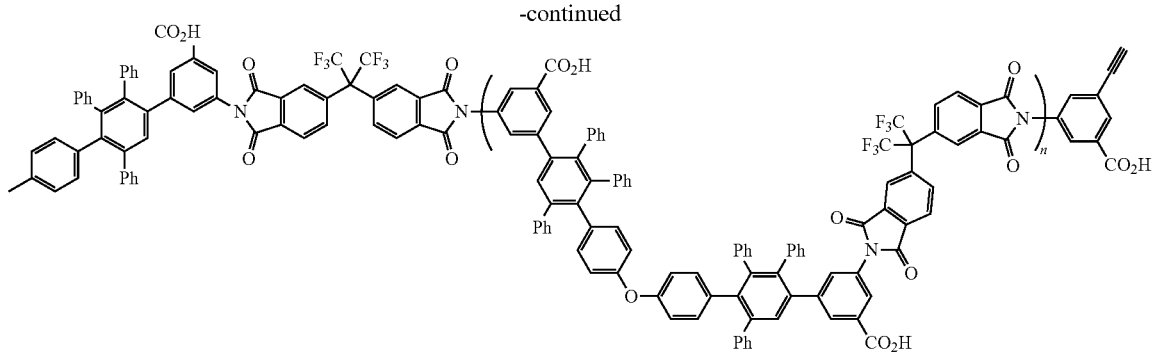

In some embodiments, the polymer compositions disclosed herein exhibit enhanced solubility in polar, protic solvents as a result of the incorporation of additional polar groups on their constituents versus incumbent polyphenylene-polyimide polymers. The functionalized bis-imide compounds and monomers, when incorporated into the copolymer compositions disclosed herein, improve material solubility without sacrificing the other desirable properties for a variety of electronics and displays applications. The specific synthetic approach disclosed herein is applicable to a broader array of polar, protic groups and therefore could find applications in other end-uses as well.

In some embodiments, the method for incorporation of polar functionalities into the monomeric constituents of the copolymer compositions disclosed herein employs a synthetic scheme based on diamine residues containing one or multiple polar groups. In some non-limiting embodiments, hydroxylated or carboxylated diamines can be used to prepare bis-imide monomers that can be reacted further to generate corresponding polymers with enhanced solubility in polar, protic solvents versus incumbent materials. In some non-limiting embodiments, the general synthetic route begins with:

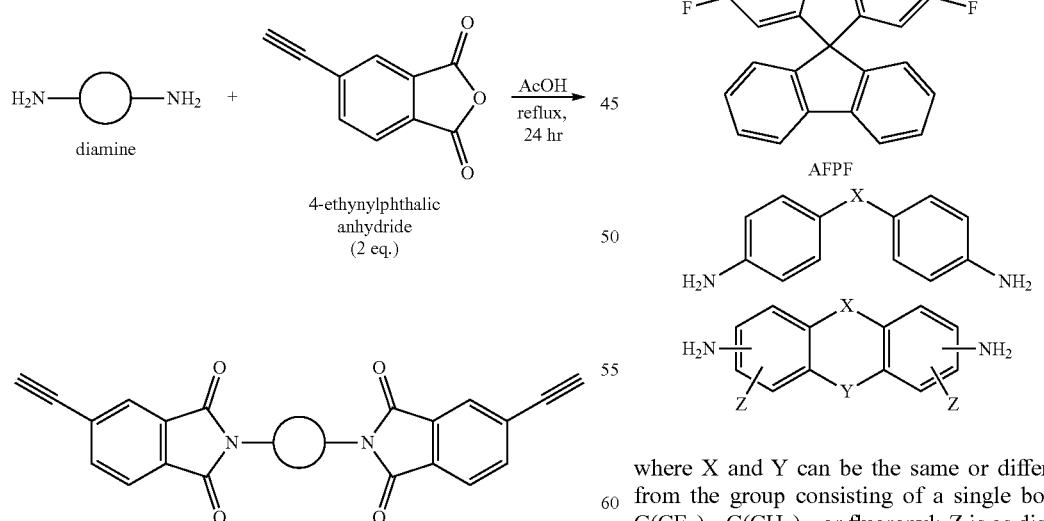

the reaction of an appropriately functionalized diamine with two equivalents of 4-ethynlphthalic anhydride to produce the desired bis-imide monomer. Some non-limiting examples of diamines with residues containing polar functional groups are:

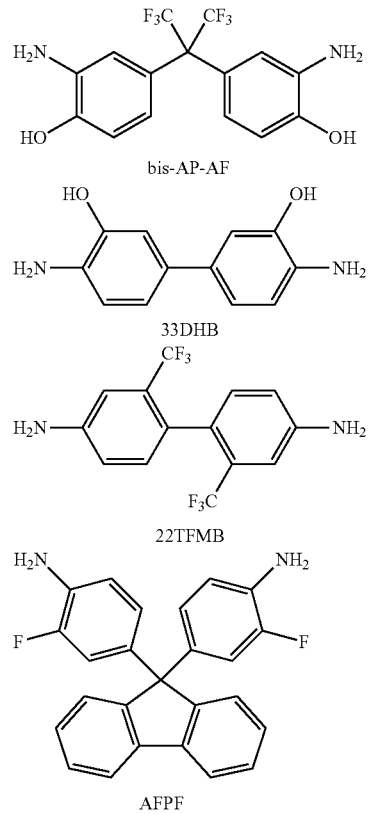

where X and Y can be the same or different and selected from the group consisting of a single bond, CO, S, $SO_2$, $C(CF_3)_2$, $C(CH_3)_2$, or fluorenyl; Z is as disclosed elsewhere herein for $Z^1$ and $Z^2$; and the like and combinations thereof, where others may be selected depending upon the material properties, solvents-of-interest, and so on.

In another non-limiting embodiment, functionalization of dianhydride monomers offers a route to the compounds and polymer compositions disclosed herein. In some non-limiting embodiments, two carboxylic acid groups are incorporated per bis-imide monomer by reacting two equivalents of AEBzOH with any number of commercially-available dianhydrides:

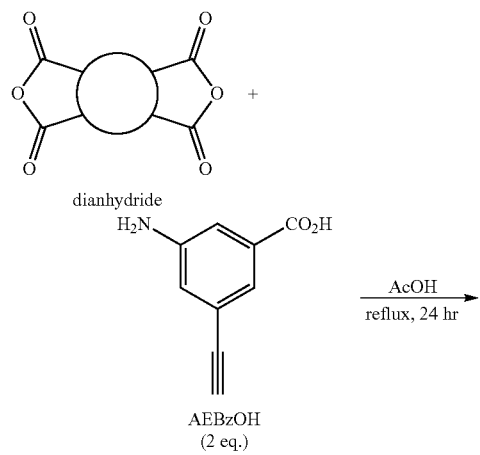

Some non-limiting examples of suitable dianhydrides include

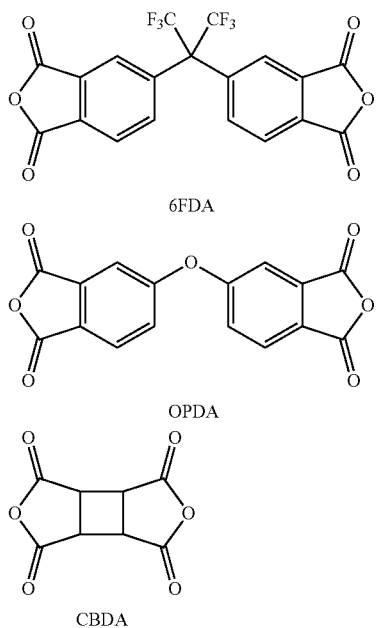

and further pyromellitic dianhydride (PMDA), 3,3',4,4'-biphenyl tetracarboxylic dianhydride (BPDA), 2,3,3',4'-biphenyl tetracarboxylic dianhydride (s-BPDA), 3,3',4,4'-benzophenone tetracarboxylic dianhydride (BTDA), bis(1,3-dioxo-1,3-dihydroisobenzofuran-5-carboxylic acid) 1,4-phenylene ester (TAHQ), 3,3',4,4'-diphenylsulfone tetracarboxylic dianhydride (DSDA), 4,4'-bisphenol-A dianhydride (BPADA), 1,3,3a, 4,5,9b-hexahydro-5 (tetrahydro-2,5-dioxo-3-furanyl) naphtho [1,2-c] tetracarboxylic dianhydride (TDA), norbornane-2-spiro-α-cyclopentanone-α'-spiro-2''-norbornane-5,5'',6,6''-tetracarboxylic dianhydride (CpODA), hydroquinone diphthalic anhydride (HQDEA), ethylene glycol bis (trimellitic anhydride) (TMEG-100), 4-(2,5-dioxotetrahydrofuran-3-yl)-1,2,3,4-tetrahydronapthalene-1,2-dicarboyxlic anhydride (DTDA), 4,4'-bisphenol A dianhydride (BPADA), xanthene tetracarboxylic dianhydride, and the like, and combinations thereof.

The compounds and polymer compositions, and their associated properties, according to the present disclosure may be prepared and used according to the examples set out below. The examples are presented herein for purposes of illustration of the present disclosure and are not intended to limit the scope of the invention described in the claims.

EXAMPLES

Synthesis Example 1

This example illustrates the preparation of a bis-imide compound having Formula 1a, Compound 1.

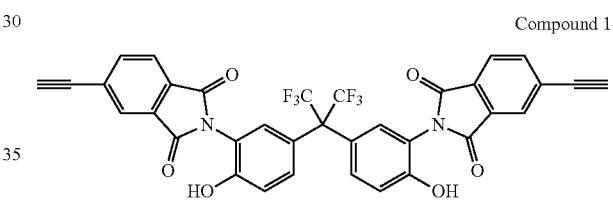

Compound 1

2,2-bis(3-amino-4-hydroxyphenyl)hexafluoropropane (bis-AP-AF) (15.00 g, 40.95 mmol, 1 eq.) and 4-etynylphthalic anhydride (14.10 g, 81.91 mmol, 2 eq.) were combined in glacial acetic acid (200 mL, 2 M bis-AP-AF) in 500 mL round-bottom flask equipped with a magnetic stir bar under nitrogen atmosphere. The round-bottom flask was fitted with a Claisen adapter affixed with a thermometer probe extending into the reaction mixture and a water-cooled condenser fitted to the side arm. The mixture temperature was increased with magnetic stirring to 118° C. (reflux) for 24 hours using a thermostatic temperature controller.

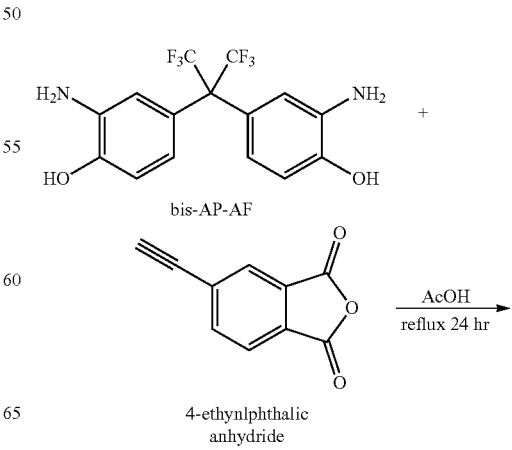

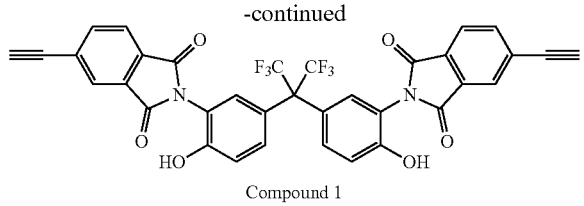

Compound 1

After cooling to room temperature, the product was precipitated by slowly dripping 100 mL portions of the reaction mixture via separatory funnel into 800 mL stirred room temperature deionized water. The solid was vacuum filtered to provide the wet product (light pinkish-white solid). The combined solid precipitates were washed with 750 mL room temperature deionized water by magnetic stirring in a 1 L beaker for 1 hour. Vacuum filtered solids were placed in a room temperature vacuum chamber and dried under high vacuum for 48 hours. The solid product (Compound 1) (24.97 g, 37.02 mmol, 90.39%) was confirmed via $^1$H and $^{13}$C NMR. If any residual acetic acid was detected, the solid was washed further with deionized water and dried. This process was repeated until no acetic acid was detected.

Synthesis Example 2

This example illustrates the preparation of a monomer having Formula 3, Compound M2-1. Compound M2-1 is an embodiment of Formula 3

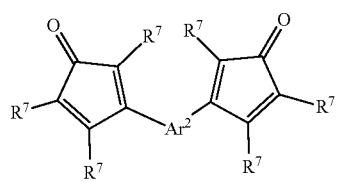

Formula 3 wherein; $R^7$=phenyl and $Ar^2$ is given by Formula 4

$$-\!\!+\!\!(Ar^3)_x\!\!+\!\!(Z\!\!-\!\!Ar^3)_y\!\!+\!\!-$$

Formula 4 wherein; $Ar^3$=phenyl, Z=O, and x=y=1. The synthesis of this material has been described in, for example, U.S. Pat. No. 5,965,679 and elsewhere. Compound M2-1 is

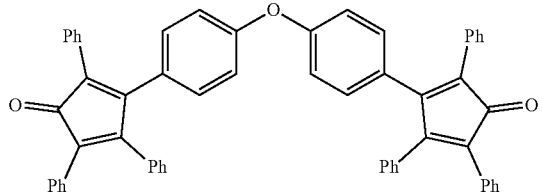

Compound M2-1

Synthesis Example 3

This example illustrates the preparation of a polymer based on bis-imide Monomer 1a and DPO-CPD, Polymer 1.

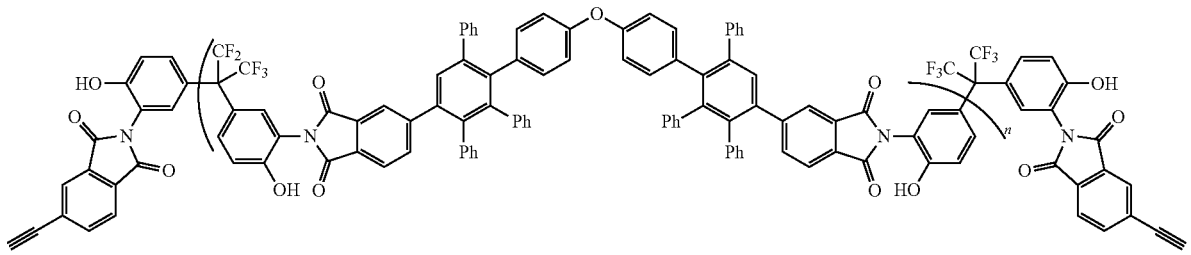

Polymer 1

Compound 1 monomer (2.000 g, 2.965 mmol, 1.1 eq.) and Compound M2-1 (2.110 g, 2.696 mmol, 1 eq.) were combined with 16 mL gamma-butryolactone (GBL) in a 50-mL round-bottom flask equipped with a magnetic stir bar under nitrogen atmosphere. The round-bottom flask was fitted with a Claisen adapter affixed with a thermometer probe extending into the reaction mixture and a water-cooled condenser fitted to the side arm. The mixture temperature was increased with magnetic stirring to 150° C. for 24 hr using a thermostatic temperature controller. After cooling to room temperature, the reaction mixture was diluted to 4 times the original volume with acetone.

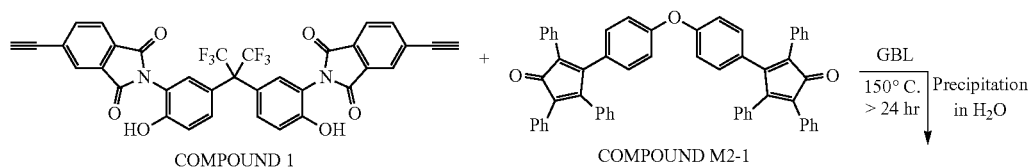

COMPOUND 1 + COMPOUND M2-1 → GBL 150° C. >24 hr | Precipitation in H$_2$O

-continued

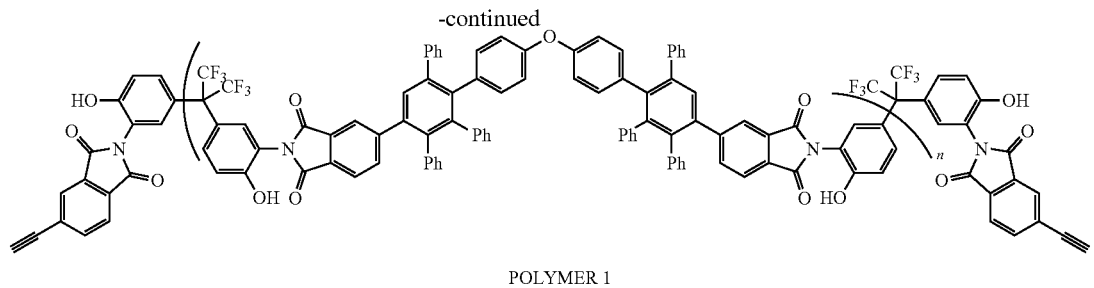

POLYMER 1

Solid polymer was precipitated slowly by dripping the diluted solution via separatory funnel into 200-mL of stirred room-temperature deionized water. The resulting cloudy suspension of solid polymer was vacuum filtered to provide the wet solid polymer that was washed with 500-mL room-temperature deionized water by stirring in a 1-L beaker for 1 hour. The solids were vacuum filtered, placed in a 60° C. heated vacuum oven, and dried under high vacuum for 48 hours. The dried polymer (3.358 g) was used for formulation and solubility shock testing. Polymer molecular weight was determined using GPC.

Synthesis Example 4

This example illustrates the preparation of a bis-imide compound having Formula 1c, Compound 16.

Compound 16

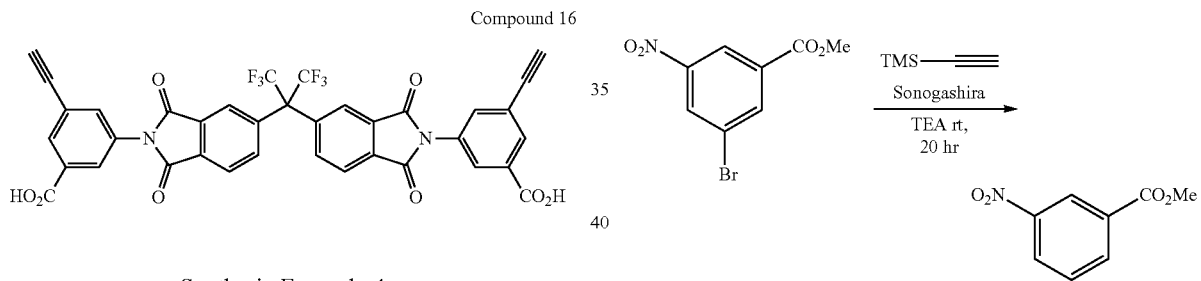

Synthesis Example 4a

Preparation of Methyl 3-bromo-5-nitrobenzoate

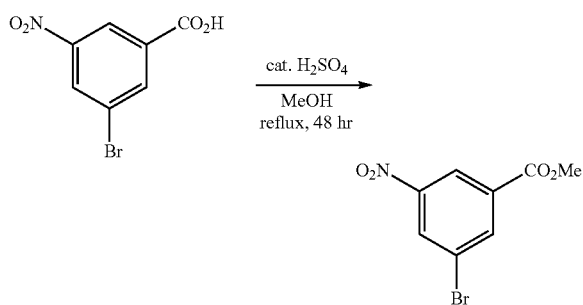

3-Bromo-5-nitrobenzoic acid (25.00 g, 98.6 mmol) was dissolved in methanol (400 mL) and 0.5 mL of sulfuric acid was added. The mixture was heated under refluxing conditions for 24 hr. A small aliquot (~1 mL) was dried on rotovap and a proton NMR was taken to assess the reaction progress. A 5-to-1 ratio of ester to acid was determined from the NMR spectrum. The reaction mixture was refluxed for an additional 24 hours at which point the conversion of acid to ester was complete as indicated by the same process. The pH was adjusted to pH 4 by addition of aqueous NaOH. Methanol was removed in-vacuo on rotavap. The crude product was extracted with 300 mL ethyl acetate, the organic phase was dried with $MgSO_4$, filtered, and concentrated in-vacuo on rotavap. Methyl 3-bromo-5-nitrobenzoate was isolated (23.17 g, 89.1 mmol, 90.38%) as a light-yellow solid which was directly used for the next step. The product was confirmed using $^1H$ NMR.

Synthesis Example 4b

Preparation of methyl 3-nitro-5-(trimethylsiliylethynyl)benzoate

Methyl 3-bromo-5-nitrobenzoate (22.88 g, 88.0 mmol, 1 eq.) from Synthesis Example 4a was dissolved in triethylamine (300 mL). Under nitrogen atmosphere, copper(I) iodide (335 mg, 1.76 mmol, 0.02 eq.) and bis(triphenylphosphine)palladium(ii) dichloride (1.235 g, 1.76 mmol; 0.02 eq.) and trimethylsilylacetylene (25 mL, 17.28 g, 175.97 mmol; 2 eq.) were added at room temperature. The mixture was stirred for 20 h at room temperature and then filtered through a silica gel plug to remove precipitated solids. The silica plug was rinsed with 50 mL ethyl acetate (flow through). The filtrate was concentrated in vacuo to remove as much triethylamine as possible. The crude residue was dissolved in 300 mL ethyl acetate and washed with 50 mL water twice and then once with 50 mL saturated sodium chloride. The organic phase was dried with $MgSO_4$, filtered and concentrated in-vacuo on rotavap. After drying on high vacuum overnight, solid methyl 3-nitro-5-(trimethylsiliylethynyl)benzoate (24.02 g, 86.6 mmol, 98.45%) was isolated and used directly for the next step. The product was confirmed using ¹H NMR.

Synthesis Example 4c

Preparation of 3-ethynyl-5-nitrobenzoic Acid

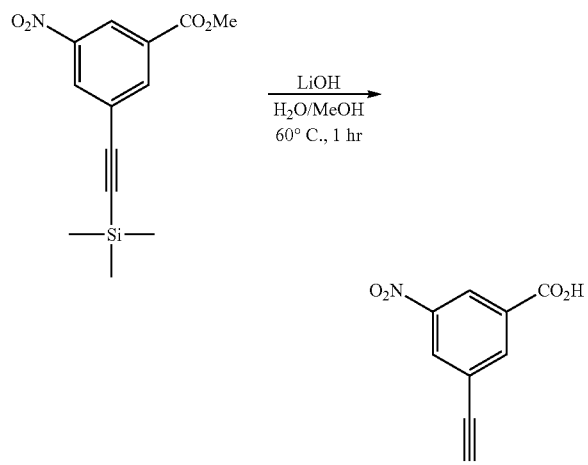

Methyl 3-nitro-5-(trimethylsiliylethynyl)benzoate (23.04 g, 83.07 mmol, 1 eq.) from Synthesis Example 4b was dissolved in methanol (300 mL) and LiOH$_{aq}$ solution (208 mL, 2 M, 416 mmol, 5 eq.) were added. The mixture was stirred for 1 h at 60° C. Reaction progress was monitored using TLC. Disappearance of starting material was observed before the end of 1-hour heating period. Next the pH was adjusted to 4 with aqueous, dilute HCl (1 M). The product was extracted with ethyl acetate, dried with MgSO₄, filtered and concentrated in-vacuo on the rotavap. Solid 3-ethynyl-5-nitrobenzoic acid (15.78 g, 82.56 mmol, 99.38%) was obtained and used directly for the next step. The crude solid retained a pink/purple color resulting from the Sonogashira reaction, and the product identity was confirmed using ¹H NMR.

Synthesis Example 4d

Preparation of 3-amino-5-ethynylbenzoic Acid

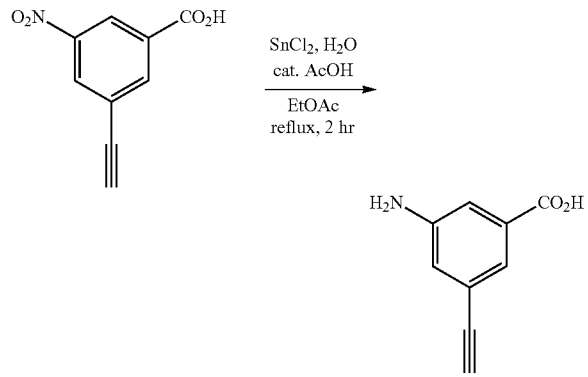

3-ethynyl-5-nitrobenzoic acid (5.00 g, 26.16 mmol, 1 eq.) from Synthesis Example 4c was dissolved in ethyl acetate (100 mL); glacial acetic acid (two drops), SnCl₂ (24.80 g, 131 mmol, 5 eq.), and water (4.7 mL, 262 mmol, 10 eq.) were added. The mixture was refluxed 2 hours before being slowly poured into ice-cold water with rapid stirring. The suspension was next adjusted to pH 5 with aqueous, saturated sodium bicarbonate (NaHCO₃). The resulting suspension was diluted with H₂O, and the product was extracted 3 times with 200 mL (each extraction) ethyl acetate. The combined organic phases were washed with water and saturated sodium chloride; and finally dried with MgSO₄, filtered, and concentrated in-vacuo on the rotavap. 3-Amino-5-ethynylbenzoic acid (2.17 g, 13.46 mmol, 51.47%) was formed as a light yellow solid, and the product was confirmed using ¹H NMR.

Synthesis Example 4e

This example illustrates the final preparation of a bis-imide compound having Formula 1c, Compound 16.

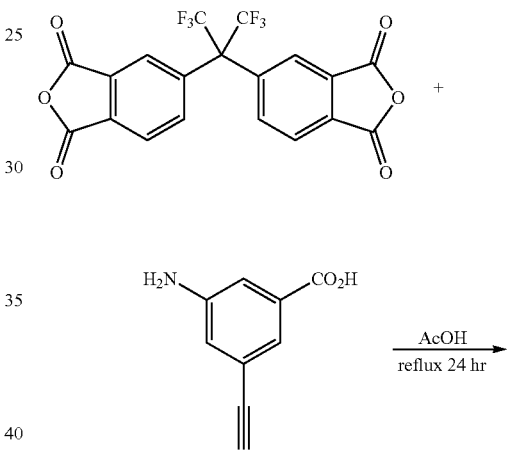

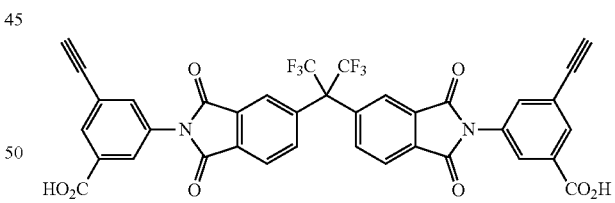

4,4'-(Hexafluoroisopropylidene)diphthalic anhydride (6FDA) (1.812 g, 4.080 mmol, 1 eq.) was combined with 3-amino-5-ethynylbenzoic acid (1.315 g, 8.160 mmol, 2 eq.) from Synthesis Example 4d in glacial acetic acid (20 mL) in a 100-mL round-bottom flask equipped with a magnetic stir bar under nitrogen atmosphere. The round-bottom flask was fitted with a Claisen adapter affixed with a thermometer probe extending into the reaction mixture and a water-cooled condenser fitted to the side arm. The mixture temperature was increased with magnetic stirring to 118° C. (reflux) for 24 hours using a thermostatic temperature controller. After cooling to room temperature, the product was precipitated by slowly dripping the reaction mixture via separatory funnel into 200-mL stirred room-temperature deionized water. The solid was vacuum filtered to provide the wet product (light pinkish-white solid). The combined solid precipitates were washed with 200-mL room-temperature deionized water by stirring in a 500-mL beaker for 1 hour. Solids were vacuum filtered, placed in room-temperature vacuum chamber, and dried under high vacuum for 48 hours. Solid monomer product (Compound 16) (2.864 g, 3.920 mmol, 96.09%) was confirmed as product using $^1$H and $^{13}$C NMR. If any residual acetic acid was detected, the solid was further washed with deionized water and dried until none was detected.

Synthesis Example 5

This example illustrates the preparation of a polymer based on bis-imide Monomer 1c and DPO-CPD, Polymer 2.

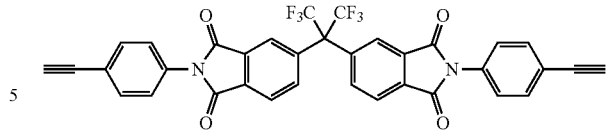

4,4'-(Hexafluoroisopropylidene)diphthalic anhydride (6FDA) (2.000 g, 4.502 mmol, 1 eq.) was combined with 4-ethynylaniline (1.055 g, 9.004 mmol, 2 eq.) in glacial acetic acid (22.5 mL) in a 100-mL round-bottom flask equipped with a magnetic stir bar under nitrogen atmo-

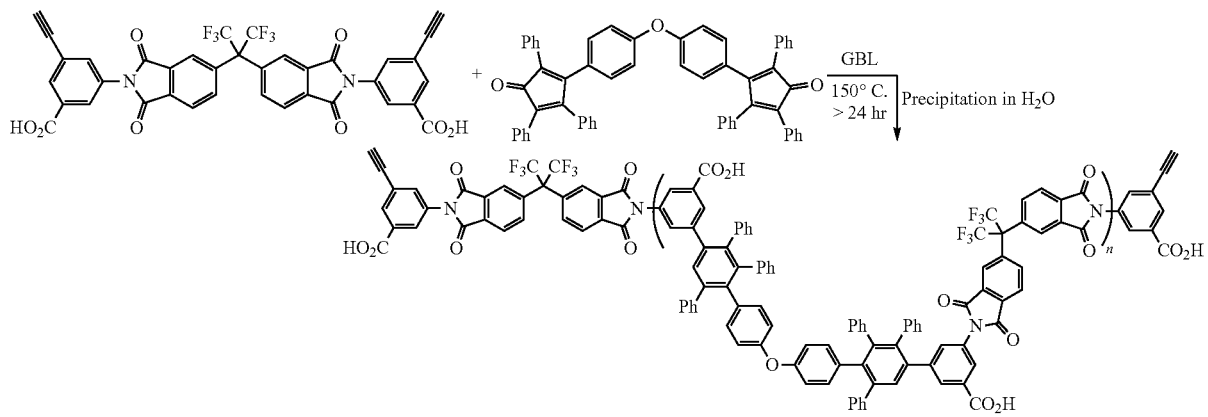

The Compound 16 monomer (2.500 g, 3.422 mmol, 1.01 eq.) prepared in Synthesis Example 4e and Compound M2-1 (DPO-CPD) (2.653 g, 2.696 mmol, 1 eq.) were combined with 25 mL gamma-butryolactone (GBL) in a 50-mL round-bottom flask equipped with a magnetic stir bar under nitrogen atmosphere. The round-bottom flask was fitted with a Claisen adapter affixed with a thermometer probe extending into the reaction mixture and a water-cooled condenser fitted to the side arm. The mixture temperature was increased with magnetic stirring to 165° C. for 24 hr using a thermostatic temperature controller. After cooling to room temperature, the reaction mixture was diluted to 4 times original volume with acetone. Solid polymer was precipitated slowly by dripping the diluted solution via separatory funnel into 200 mL stirred room-temperature deionized water. The resulting cloudy suspension of solid polymer was vacuum filtered to provide the wet solid polymer that was washed with 500 mL room-temperature deionized water by stirring in a 1 L beaker for 1 hour. The solids were vacuum filtered, placed in a 60° C. heated vacuum oven, and dried under high vacuum for 48 hours. The dried polymer (3.641 g) was used in next step for formulation and solubility shock testing. Polymer molecular weight was determined using GPC.

Comparative Example Synthesis 1

This example illustrates the preparation of a comparative bis-imide compound, Compound A.

sphere. The round-bottom flask was fitted with a Claisen adapter affixed with a thermometer probe extending into the reaction mixture and a water-cooled condenser fitted to the side arm. The mixture temperature was increased with magnetic stirring to 118° C. (reflux) for 6 hours using a thermostatic temperature controller. After cooling to room temperature, the product was precipitated by slowly dripping the reaction mixture via separatory funnel into 200-mL stirred room-temperature deionized water. The solid was vacuum filtered to provide the wet product (white solid). The solid precipitate was washed with 200-mL room-temperature deionized water by stirring in a 500-mL beaker for 1 hour. Solids were vacuum filtered, placed in room-temperature vacuum chamber, and dried under high vacuum for 48 hours. Solid monomer product (2.775 g, 4.319 mmol, 95.9%) was confirmed as product using $^1$H and $^{13}$C NMR. If any residual acetic acid was detected, the solid was further washed with deionized water and dried until none was detected.

Comparative Synthesis Example 2

This example illustrates the preparation of a polymer based on bis-imide Compound A and DPO-CPD, Comparative Polymer A.

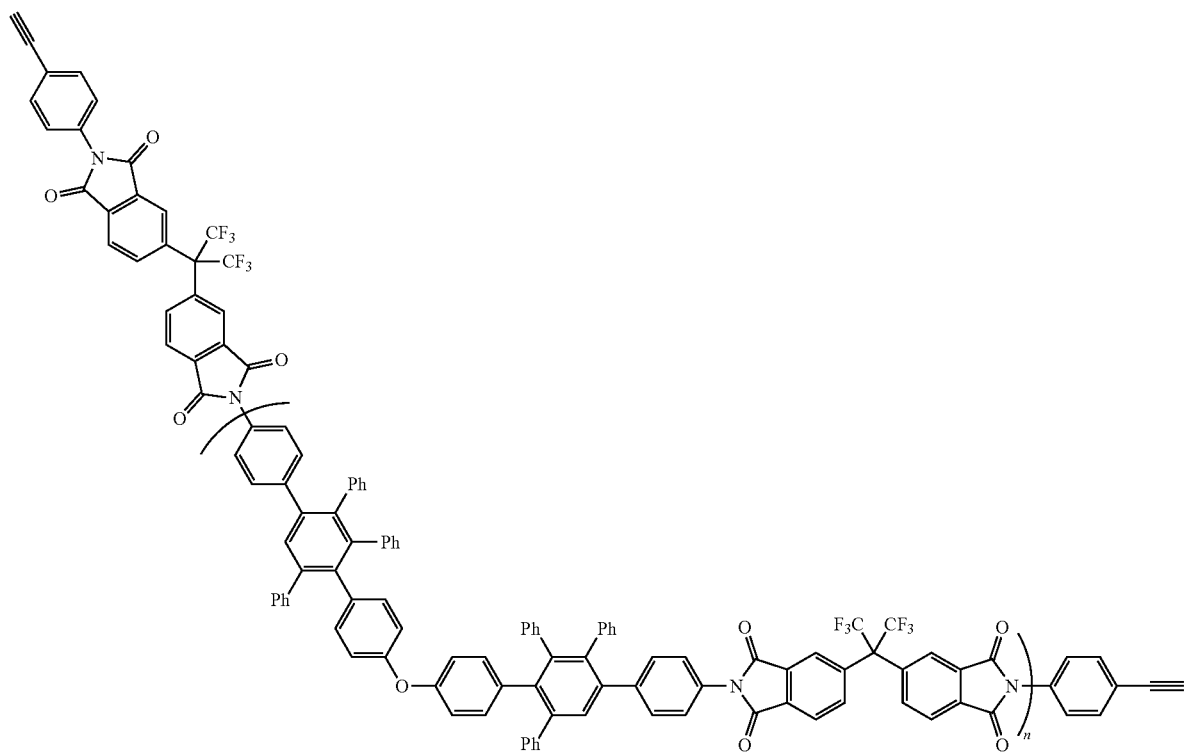

The Compound A monomer (2.000 g, 3.113 mmol, 1.01 eq.) prepared in Comparative Example Synthesis 1 and Compound M2-1 (DPO-CPD) (2.412 g, 3.082 mmol, 1 eq.) were combined with 25 mL gamma-butyrolactone (GBL) in a 50-mL round-bottom flask equipped with a magnetic stir bar under nitrogen atmosphere. The round-bottom flask was fitted with a Claisen adapter affixed with a thermometer probe extending into the reaction mixture and a water-cooled condenser fitted to the side arm. The mixture temperature was increased with magnetic stirring to 165° C. for 24 hr using a thermostatic temperature controller. After cooling to room temperature, the reaction mixture was diluted to 4 times original volume with acetone. Solid polymer was precipitated slowly by dripping the diluted solution via separatory funnel into 200 mL stirred room-temperature deionized water. The resulting cloudy suspension of solid polymer was vacuum filtered to provide the wet solid polymer that was washed with 500 mL room-temperature deionized water by stirring in a 1 L beaker for 1 hour. The solids were vacuum filtered, placed in a 60° C. heated vacuum oven, and dried under high vacuum for 48 hours. The dried polymer (3.742 g) was used in next step for formulation and solubility shock testing. Polymer molecular weight was determined using GPC.

Comparative Example Synthesis 3

This example illustrates the preparation of a comparative bis-imide compound, Compound B.

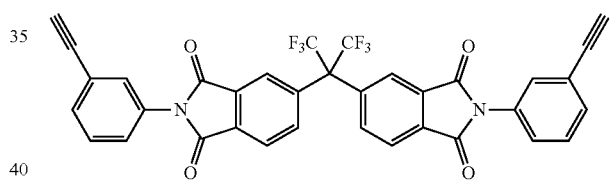

4,4'-(Hexafluoroisopropylidene)diphthalic anhydride (6FDA) (5.000 g, 20.935 mmol, 1 eq.) was combined with 3-ethynylaniline (5.000 g, 41.869 mmol, 2 eq.) in glacial acetic acid (84 mL) in a 250-mL round-bottom flask equipped with a magnetic stir bar under nitrogen atmosphere. The round-bottom flask was fitted with a Claisen adapter affixed with a thermometer probe extending into the reaction mixture and a water-cooled condenser fitted to the side arm. The mixture temperature was increased with magnetic stirring to 118° C. (reflux) for 6 hours using a thermostatic temperature controller. After cooling to room temperature, the product was precipitated by slowly dripping the reaction mixture via separatory funnel into 200-mL stirred room-temperature deionized water. The solid was vacuum filtered to provide the wet product (white solid). The solid precipitate was washed with 200-mL room-temperature deionized water by stirring in a 500-mL beaker for 1 hour. Solids were vacuum filtered, placed in room-temperature vacuum chamber, and dried under high vacuum for 48 hours. Solid monomer product (12.50 g, 19.455 mmol, 92.9%) was confirmed as product using $^1$H and $^{13}$C NMR. If any residual acetic acid was detected, the solid was further washed with deionized water and dried until none was detected.

Comparative Synthesis Example 4

This example illustrates the preparation of a polymer based on bis-imide Compound B and DPO-CPD, Comparative Polymer B.

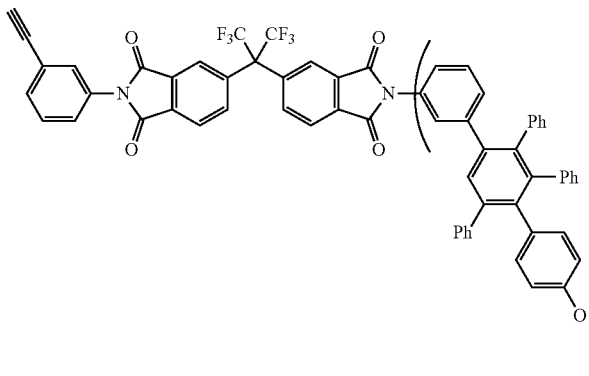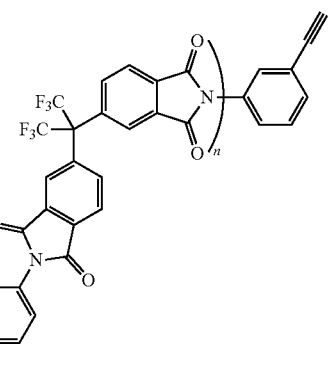

The monomer (10.000 g, 15.564 mmol, 1.025 eq.) prepared in Comparative Example 3 and Compound M2-1 (11.888 g, 15.184 mmol, 1 eq.) were combined with 75 mL gamma-butyrolactone (GBL) in a 250-mL round-bottom flask equipped with a magnetic stir bar under nitrogen atmosphere. The round-bottom flask was fitted with a Claisen adapter affixed with a thermometer probe extending into the reaction mixture and a water-cooled condenser fitted to the side arm. The mixture temperature was increased with magnetic stirring to 165° C. for 24 hr using a thermostatic temperature controller. After cooling to room temperature, the reaction mixture was diluted to 4 times original volume with acetone. Solid polymer was precipitated slowly by dripping the diluted solution via separatory funnel into 1 L stirred room-temperature deionized water. The resulting cloudy suspension of solid polymer was vacuum filtered to provide the wet solid polymer that was washed with 500 mL room-temperature deionized water by stirring in a 1 L beaker for 1 hour. The solids were vacuum filtered, placed in a 60° C. heated vacuum oven, and dried under high vacuum for 48 hours. The dried polymer (18.665 g) was used in next step for formulation and solubility shock testing. Polymer molecular weight was determined using GPC.

Solubility Examples

Polymer solubility was assessed via subjecting formulations to shock tests to determine their compatibility with solvent systems that are commonly used in the electronics and displays industries. Polymers were formulated first in a solvent system of methyl 3-methoxypropionate (MMP), anisole, and gamma-butyrolactone (GBL) in a 61.75:33.25:5 ratio at either 12 or 30 wt % solid polymer concentration and then filtered through a 0.2 μm PTFE filter. More viscous solutions were filtered through 0.45 μm PTFE or 5 μm Nylon filters. The test-solvent system was composed of propylene glycol monomethyl ether (PGME) and propylene glycol monomethyl ether acetate (PGMEA) in a 70:30 ratio. Shock testing was performed by attempting to dissolve and dilute a small amount of polymer formulation by 30:1 and 200:1 with the test-solvent system. Mixtures were then rolled to mix. Next, solubility ratings were assigned based on the following criteria in Table 1 below for visual inspections of both dilutions. In some embodiments, requirements-in-use place a threshold of acceptability at a shock test rating of 4.5.

TABLE 1

Rating system for assigning shock test solubility values based on visual inspection.

| Rating | Cloudiness | Precipitation |
|---|---|---|
| 1 | N/A | Complete precipitation; immiscible; no mixing |
| 2 | Very Cloudy, Opaque | Significant portion of formulation precipitates |
| 3 | Slightly Cloudy, Translucent | Some precipitation; many particulates |
| 4 | Nearly Clear, Slightly Hazy | Marginal precipitation; few particulates |
| 4.5 | Clear, Transparent | Marginal precipitation; few particulates |
| 5 | Clear, Transparent | No precipitation; completely soluble |

Representative results for the polymers disclosed herein are summarized in Table 2.

TABLE 2

Comparison of shock test values of polymers disclosed herein with previous para-FPL polymers. Included for reference are molecular weight data and formulated solid polymer concentrations for each shock test rating.

| | | | | Shock Test Rating | |
|---|---|---|---|---|---|
| Example | Monomers | Mw | PDI | 30:1 dilution | 200:1 dilution |
| Comparative Polymer A | Compound A + Compound M2-1 | 17,976 | 2.331 | 3 @ 30 wt % 3.5 @ 15 wt % | 3 @ 30 wt % 4 @ 15 wt % |

TABLE 2-continued

Comparison of shock test values of polymers disclosed herein with previous para-FPL polymers. Included for reference are molecular weight data and formulated solid polymer concentrations for each shock test rating.

| Example | Monomers | Mw | PDI | Shock Test Rating 30:1 dilution | 200:1 dilution |
|---|---|---|---|---|---|
| Comparative Polymer B | Compound B + Compound M2-1 | 33,608 | 3.356 | 1 @ 15 wt % | 1.5 @ 15 wt % |
| Polymer 2 | Compound 2 + Compound M2-1 | 18,923 | 2.690 | 4.5 @ 12 wt % | 4.5 @ 12 wt % |
| Polymer 1 | Compound 1 + Compound M2-1 | 24,430 | 3.425 | 4.5 @ 12 wt % | 4.5 @ 12 wt % |
| Polymer 1 | Compound 1 + Compound M2-1 | 59,004 | 3.159 | 4.5 @ 30 wt % 4.5 @ 12 wt % | 4.5 @ 30 wt % 4.5 @ 12 wt % |

Both Polymer 1 and Polymer 2 are found to exhibit improved solubility vs. Comparative Polymer A and Comparative Polymer B in the solvent systems disclosed herein. Further, higher-molecular-weight variants of these polymers retain favorable solubility properties in solvents of interest.

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

It is to be appreciated that certain features are, for clarity, described herein in the context of separate embodiments, may also be provided in combination in a single embodiment. Conversely, various features that are, for brevity, described in the context of a single embodiment, may also be provided separately or in any subcombination. The use of numerical values in the various ranges specified herein is stated as approximations as though the minimum and maximum values within the stated ranges were both being preceded by the word "about." In this manner, slight variations above and below the stated ranges can be used to achieve substantially the same results as values within the ranges. Also, the disclosure of these ranges is intended as a continuous range including every value between the minimum and maximum average values including fractional values that can result when some of components of one value are mixed with those of different value. Moreover, when broader and narrower ranges are disclosed, it is within the contemplation of this invention to match a minimum value from one range with a maximum value from another range and vice versa.

What is claimed is:

1. A polymer composition comprising a copolymer polymerized from a monomer mixture of (a) one or more first monomers comprising a bis-imide compound comprising two or more aryl moieties substituted with ethynyl moieties and the two or more aryl moieties each having one or more polar substituents; and (b) one or more second monomers comprising two or more cyclopentadienone moieties;

wherein the one or more first monomers is a compound having Formula 1a,

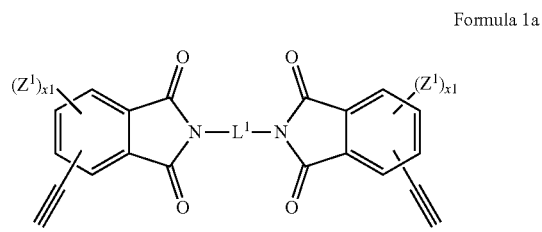

Formula 1a wherein:
  $L^1$ is a divalent aromatic linking group substituted with $(Z^2)_y$;
  $Z^1$ and $Z^2$ are the same or different at each occurrence and are polar groups;
  x1 is 0; and
  y is 1.

2. The polymer composition of claim 1, wherein the one or more second monomers has Formula 3,

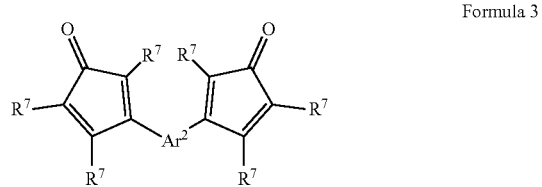

Formula 3 wherein:
R[7] is the same or different at each occurrence and is a substituted or unsubstituted $C_{6-20}$ aryl,
and:
Ar[2] is a substituted or unsubstituted $C_{6-20}$ aryl group.

3. The polymer composition of claim 2, wherein Ar[2] has Formula 4,

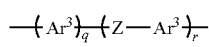

Formula 4 wherein:
q is 1;
r is 1;
Ar[3] is Formula 5,

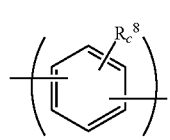

Formula 5 wherein:
R[8] is the same or different at each occurrence and is selected from the group consisting of halogen, substituted or unsubstituted $C_{1-6}$ alkyl, aryl, and aryloxy;
c is 0; and
Z is O.

4. The polymer composition of claim 1, wherein the one or more second monomers is Compound M2-1

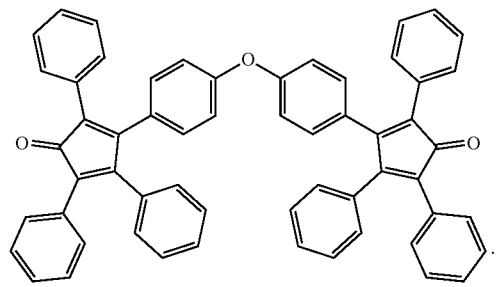

5. The polymer composition of claim 1, wherein the copolymer is

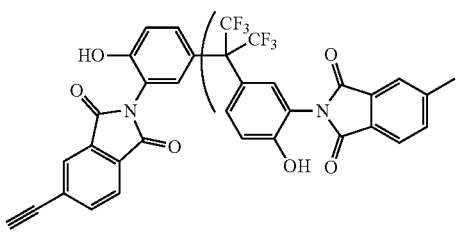

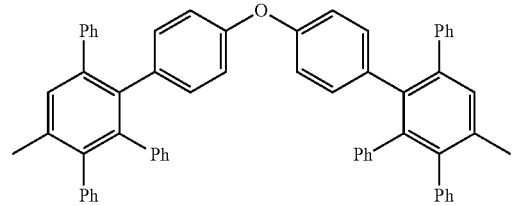

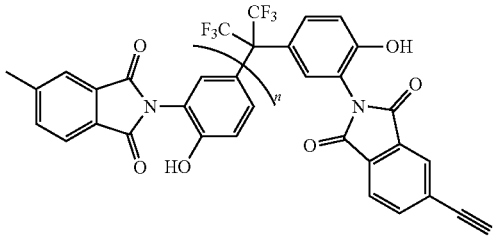

wherein 15<n<50.

* * * * *